(12) United States Patent
Borkholder et al.

(10) Patent No.: US 11,969,229 B2
(45) Date of Patent: Apr. 30, 2024

(54) SYSTEMS, DEVICES, AND METHODS FOR MEASURING BODY TEMPERATURE OF A SUBJECT USING CHARACTERIZATION OF FECES AND/OR URINE

(71) Applicant: Casana Care, Inc., Rochester, NY (US)

(72) Inventors: David A. Borkholder, Canandaigua, NY (US); Hamed Shamkhalichenar, Rochester, NY (US)

(73) Assignee: Casana Care, Inc., Rochester, NY (US)

( * ) Notice: Subject to any disclaimer, the term of this patent is extended or adjusted under 35 U.S.C. 154(b) by 0 days.

(21) Appl. No.: 17/851,938

(22) Filed: Jun. 28, 2022

(65) Prior Publication Data

US 2022/0361754 A1 Nov. 17, 2022

Related U.S. Application Data

(63) Continuation of application No. PCT/US2022/029646, filed on May 17, 2022.
(Continued)

(51) Int. Cl.
*A61B 5/00* (2006.01)
*A61B 5/01* (2006.01)
(Continued)

(52) U.S. Cl.
CPC .............. *A61B 5/0008* (2013.01); *A61B 5/01* (2013.01); *A61B 5/6891* (2013.01);
(Continued)

(58) Field of Classification Search
CPC ....... A61B 5/01; A61B 5/0008; A61B 5/6891; A61B 5/6886; A61B 5/7264; G01K 13/223
See application file for complete search history.

(56) References Cited

U.S. PATENT DOCUMENTS

| | | |
|---|---|---|
| 4,203,497 A | 5/1980 | Harris et al. |
| 4,212,361 A | 7/1980 | Stocker |

(Continued)

FOREIGN PATENT DOCUMENTS

| | | |
|---|---|---|
| CA | 1324415 C | 11/1993 |
| CN | 100502773 C | 6/2009 |

(Continued)

OTHER PUBLICATIONS

Non-Final Office Action mailed Jan. 26, 2017 for U.S. Appl. No. 15/190,534, 6 pages.
(Continued)

*Primary Examiner* — Devin B Henson
(74) *Attorney, Agent, or Firm* — Cooley LLP

(57) ABSTRACT

Systems, devices, and methods are disclosed herein for monitoring physiological data of subjects urinating or defecating into an excretion collection device, including systems, devices, and methods for monitoring temperature of objects (e.g., urine or feces) received through the opening of the excretion collection device. In some embodiments, systems, devices, and methods disclosed herein include a temperature sensor that can generate a temperature profile associated with a urination or defecation event, and determine a core body temperature of a subject based on the temperature profile.

38 Claims, 14 Drawing Sheets

Related U.S. Application Data

(60) Provisional application No. 63/291,615, filed on Dec. 20, 2021, provisional application No. 63/189,539, filed on May 17, 2021.

(51) Int. Cl.
*A61B 10/00* (2006.01)
*G01N 33/483* (2006.01)

(52) U.S. Cl.
CPC ........ *A61B 10/0038* (2013.01); *A61B 10/007* (2013.01); *G01N 33/483* (2013.01)

(56) References Cited

U.S. PATENT DOCUMENTS

| | | | |
|---|---|---|---|
| 4,697,656 | A | 10/1987 | de Canecaude |
| 4,711,313 | A | 12/1987 | Lida et al. |
| 4,969,112 | A | 11/1990 | Castle |
| 6,727,438 | B1 | 4/2004 | Stokes |
| 7,437,781 | B2 | 10/2008 | Rigas |
| 7,521,638 | B1 | 4/2009 | Godshaw et al. |
| 8,827,918 | B2 | 9/2014 | Kim et al. |
| 8,983,854 | B2 | 3/2015 | Park et al. |
| 9,595,185 | B1 | 3/2017 | Hall et al. |
| 9,829,311 | B1 | 11/2017 | Wilson et al. |
| 9,927,302 | B1 | 3/2018 | Hall et al. |
| 10,292,658 | B2 | 5/2019 | Borkholder et al. |
| 11,234,651 | B2 | 2/2022 | Borkholder et al. |
| 11,650,094 | B2 | 5/2023 | Borkholder et al. |
| 2002/0188205 | A1 | 12/2002 | Mills |
| 2003/0233034 | A1 | 12/2003 | Varri et al. |
| 2004/0112149 | A1 | 6/2004 | Gebert |
| 2005/0228305 | A1 | 10/2005 | Nagata et al. |
| 2006/0111641 | A1 | 5/2006 | Manera et al. |
| 2006/0258915 | A1 | 11/2006 | Shiegek Ueda et al. |
| 2008/0194975 | A1 | 8/2008 | MacQuarrie et al. |
| 2010/0094147 | A1 | 4/2010 | Inan et al. |
| 2013/0310700 | A1 | 11/2013 | Wiard et al. |
| 2014/0039301 | A1 | 2/2014 | Seo et al. |
| 2014/0142396 | A1 | 5/2014 | Ricks et al. |
| 2014/0142437 | A1 | 5/2014 | Inan et al. |
| 2014/0142451 | A1 | 5/2014 | Kim et al. |
| 2016/0317043 | A1 | 11/2016 | Campo et al. |
| 2016/0331244 | A1* | 11/2016 | Barton-Sweeney ..... A61B 5/01 |
| 2016/0374618 | A1 | 12/2016 | Giovangrandi |
| 2016/0374619 | A1 | 12/2016 | Borkholder et al. |
| 2017/0172421 | A1 | 6/2017 | Dabby et al. |
| 2018/0020984 | A1 | 1/2018 | Hall et al. |
| 2018/0042386 | A1 | 2/2018 | Hall et al. |
| 2018/0084960 | A1 | 3/2018 | Iwabata et al. |
| 2018/0153414 | A1* | 6/2018 | Hall ..................... A61B 5/0082 |
| 2019/0008457 | A1 | 1/2019 | Hall et al. |
| 2019/0178704 | A1 | 6/2019 | Lui |
| 2019/0231271 | A1 | 8/2019 | Borkholder et al. |
| 2019/0298316 | A1 | 10/2019 | Kashyap et al. |
| 2020/0289000 | A1 | 9/2020 | Hall et al. |
| 2020/0390367 | A1 | 12/2020 | Hall et al. |
| 2020/0390422 | A1 | 12/2020 | Hall et al. |
| 2022/0218286 | A1 | 7/2022 | Borkholder et al. |
| 2022/0346720 | A1* | 11/2022 | David .................. A61B 5/0507 |
| 2022/0364904 | A1 | 11/2022 | Borkholder et al. |
| 2022/0378373 | A1 | 12/2022 | Conn |
| 2023/0240485 | A1 | 8/2023 | Kashyap et al. |
| 2024/0027255 | A1 | 1/2024 | Borkholder et al. |

FOREIGN PATENT DOCUMENTS

| | | |
|---|---|---|
| CN | 102660988 B | 9/2012 |
| CN | 203042108 U | 7/2013 |
| CN | 210 123 304 U | 3/2020 |
| DE | 10 2010 061 035 A1 | 6/2012 |
| EP | 1 488 739 A1 | 12/2004 |
| JP | H04-367638 A | 12/1992 |
| JP | 2000-254040 A1 | 9/2000 |
| JP | 2010172498 A | 8/2010 |
| JP | 2020-153896 A | 9/2020 |
| KR | 2017/0125696 A | 11/2017 |
| WO | WO 2005/070288 A1 | 8/2005 |
| WO | WO-2020172645 A1 | 8/2020 |
| WO | WO 2021/055681 A1 | 3/2021 |

OTHER PUBLICATIONS

Final Office Action mailed Oct. 6, 2017 for U.S. Appl. No. 15/190,534, 6 pages.

Non-Final Office Action mailed Feb. 22, 2018 for U.S. Appl. No. 15/190,534, 9 pages.

Final Office Action mailed Sep. 4, 2018 for U.S. Appl. No. 15/190,534, 9 pages.

Advisory Action mailed Nov. 13, 2018 for U.S. Appl. No. 15/190,534, 4 pages.

Non-Final Office Action mailed Jul. 6, 2020 for U.S. Appl. No. 16/377,938, 10 pages.

Non-Final Office Action mailed Dec. 1, 2020 for U.S. Appl. No. 16/377,938, 9 pages.

Invitation to Pay Additional Fees mailed Jul. 20, 2022 for International Application No. PCT/US2022/024236, 21 pages.

International Search Report and Written Opinion mailed Aug. 5, 2022 for International Application No. PCT/US2022/028787, 23 pages.

Arias, D. E. et al., "Data collection capabilities of a new non-invasive monitoring system for patients with advanced multiple sclerosis," AMIA Annual Symposium Proceedings, 2013:61-68 (2013).

Baek, H. J. et al., "System for Unconstrained ECG Measurement on a Toilet Seat using Capacitive Coupled Electrodes: The Efficacy and Practicality," Annu Int Conf IEEE Eng Med Biol Soc., Aug. 20-24, 2008; pp. 2326-2328, Vancouver, British Columbia, Canada.

Chen, Z. et al., "Noninvasive Monitoring of Blood Pressure Using Optical Ballistocardiography and Photoplethysmograph Approaches," 35th Annual International Conference of the IEEE EMBS, Jul. 3-7, 2013, pp. 2425-2428, Osaka, Japan.

Huang, J.-J. et al., "Development of the smart toilet equipment with measurements of physiological parameters," 2012 9th International Conference on Ubiquitous Intelligence and Computer and 9th International Conference on Autonomous and Trusted Computing, 2012, pp. 9-16; doi:10.1109/UIC-ATC.2012.143.

Inan, O. T. et al., "Robust ballistocardiogram acquisition for home monitoring," Physiol Meas, 30(2):169-85 (2009); doi:10.1088/0967-3334/30/2/005.

Javaid, A. Q. et al., "Quantifying and Reducing Posture-Dependent Distortion in Ballistocardiogram Measurements," IEEE Journal of Biomedical and Health Informatics, 19(5):1549-1556 (2015).

Junnila, S. et al., "An EMFi-film sensor based ballistocardiographic chair: performance and cycle extraction method," IEEE Workshop on Signal Processing Systems Design and Implementation, 2005, pp. 373-377.

Kim, J. S. et al., "Multi-channel measurement of photoplethysmography and evaluation for the optimal site of a thigh in a toilet," 26th Annual International Conference of the IEEE, Sep. 1-5, 2004, pp. 3366-3368, San Francisco, California, USA.

Kim, K. K. et al., "The electrically noncontacting ECG measurement on the toilet seat using the capacitively-coupled insulated electrodes," The 26th Annual International Conference of the IEEE Engineering in Medicine and Biology Society, San Francisco, CA, USA, 2004, pp. 2375-2378, doi:10.1109/IEMBS.2004.1403688.

Kim, J. S. et al., "A new approach for non-intrusive monitoring of blood pressure on a toilet seat," Physiological Measurement, 27:203-211 (2006).

Lim, Y.G. et al., "Capacitive Measurement of ECG for Ubiquitous Healthcare," Annals of Biomedical Engineering, 42(11):2218-2227 (2014).

Motoi, K. et al., "Development and Clinical Evaluation of a Home Healthcare System Measuring in Toilet, Bathtub and Bed without Attachment of Any Biological Sensors," Proceedings of the 10th

(56) References Cited

OTHER PUBLICATIONS

IEEE International Conference on Information Technology and Applications in Biomedicine, Corfu, Greece, 2010, pp. 1-4, doi:10.1109/ITAB.2010.5687774.
Motoi, K. et al., "Development of a fully automated network system for long-term health-care monitoring at home," Proceedings of the 29th Annual International Conference of the IEEE EMBS, Aug. 23-26, 2007, pp. 1826-1829, Cite Internationale, Lyon, France.
Park, K. S., "Nonintrusive Measurement of Biological Signals for Ubiquitous Healthcare," 31st Annual International Conference of the IEEE EMBS, Sep. 2-6, 2009, pp. 6573-6575, Minneapolis, Minnesota, USA.
Prisk, G. K. et al., "Three-dimensional ballistocardiography and respiratory motion in sustained microgravity," Aviation Space and Environmental Medicine, 72(12):1067-1074 (2002).
Schlebusch, T., "Unobtrusive Health Screening on an Intelligent Toilet Seat," ACTA Polytechnica, 51(5):94-99 (2011); http://www.tk.de/tk/innovative-verfahren/telemedizin/herz/9784.
Shin, J. H. et al., "Ubiquitous House and Unconstrained Monitoring Devices for Home Healthcare System," 2007 6th International Special Topic Conference on Information Technology Applications in Biomedicine, Tokyo, Japan, 2007, pp. 201-204, doi:10.1109/ITAB.2007.4407381.
Tanaka, S. et al., "Fully Automatic System for Monitoring Blood Pressure from a Toilet Seat Using Volume-Oscillometric Method," Proceedings of the 2005 IEEE Engineering in Medicine and Biology, 27th Annual Conference, Sep. 1-4, 2005, pp. 3939-3941, Shanghai, China.
Tavakolian, K. et al., "Comparative analysis of infrasonic cardiac signals," Computers in Cardiology, 36:757-760 (2009).
Togawa, T. et al., "Physiological Monitoring Systems Attached to the Bed and Sanitary Equipment," Images of the Twenty-First Century. Proceedings of the Annual International Engineering in Medicine and Biology Society, Seattle, WA, USA, 1989, pp. 1461-1463 vol.5, doi: 10.1109/IEMBS.1989.96289.
Weber, T. et al., "Noninvasive determination of carotid-femoral pulse wave velocity depends critically on assessment of travel distance: a comparison with invasive measurement," Journal of Hypertension, 27(8):1624-1630 (2009).
Yamakoshi, K. et al., "Non-conscious and Automatic Acquisition of body and Excreta Weight Together with Ballistocardiogram in a Lavatory," 18th Annual International Conference of the IEEE Engineering in Medicine and Biology Society, 1996, pp. 67-68, Amsterdam, 1.1.6:Home Health Monitoring.
International Search Report and Written Opinion mailed Sep. 12, 2022 for International Application No. PCT/US2022/024236, 24 pages.
Invitation to Pay Additional Fees mailed Sep. 9, 2022 for International Application No. PCT/US2022/029646, 15 pages.
International Search Report and Written Opinion for Application No. PCTUS2022029646, mailed on Nov. 3, 2022, 23 pages.
Non-Final Office Action for U.S. Appl. No. 17/885,299 dated Jul. 17, 2023, 21 pages.
Non-Final Office Action mailed Aug. 16, 2023 for U.S. Appl. No. 17/557,264, 21 pages.
Final Office Action for U.S. Appl. No. 17/885,299, filed Dec. 21, 2023, 12 pages.
Non-Final Office Action for U.S. Appl. No. 18/130,286, filed Feb. 15, 2024, 9 pages.
Non-Final Office Action mailed Sep. 15, 2022 for U.S. Appl. No. 17/845,883, 11 pages.

\* cited by examiner

SYSTEMS, DEVICES, AND METHODS FOR MEASURING BODY TEMPERATURE OF A SUBJECT USING CHARACTERIZATION OF FECES AND/OR URINE

CROSS-REFERENCE TO RELATED APPLICATIONS

This application is a continuation of International Patent Application No. PCT/US2022/029646, entitled "Systems, Devices, and Methods for Measuring Body Temperature of a Subject Using Characterization of Feces and/or Urine," filed May 17, 2022, which claims the benefit of U.S. Provisional Patent Application Ser. No. 63/189,539, entitled "Systems, Devices, and Methods for Measurement of Human Body Core Temperature Using Urine or Feces," filed May 17, 2021, and U.S. Provisional Patent Application Ser. No. 63/291,615, entitled "Systems, Devices, and Methods for Measuring Body Temperature of a Subject Using Characterization of Feces and/or Urine," filed Dec. 20, 2021, the disclosures of which are incorporated by reference herein in their entireties.

TECHNICAL FIELD

The embodiments described herein relate generally to health monitoring systems, and more particularly to systems and methods for measuring body temperature through the characterization of urine and/or feces.

BACKGROUND

Patient health monitoring is an important tool in tracking physiological conditions of patients and to provide early warnings or guidance to individuals and healthcare providers in cases of patient health deterioration. Oftentimes, patient monitoring is obtrusive and requires individuals to actively wear certain devices or change their routine to be able to measure certain vital signs or characteristics of the patient. Unobtrusive systems for monitoring individuals are also limited and can provide inaccurate results. Therefore, there exists a need to develop more accurate approaches to monitoring individuals through unobtrusive means.

SUMMARY

Systems, devices, and methods are described herein for measuring data of individuals during urination and/or defecation, e.g., using a toilet, urinal, latrine, or other excretion collection device or waste receptacle.

In some embodiments, an apparatus includes: a housing including a coupler configured to couple to a toilet; a temperature sensor supported by the housing, the temperature sensor oriented toward an opening of the toilet when the coupler is coupled to the toilet such that the temperature sensor can measure a temperature of urine or feces of a subject seated on the toilet as the urine or feces is received through the opening of the toilet; and a processor operatively coupled to the temperature sensor, the processor configured to: receive temperature data indicative of the temperature of the urine or feces from the temperature sensor; and determine a core body temperature of the subject based on the temperature data.

In some embodiments, a method includes: detecting a urination or defecation event at a toilet; in response to detecting the urination or defecation event, activating a temperature sensor, the temperature sensor being coupled to the toilet and orientated to face an opening of the toilet for receiving urine or feces of a subject; collecting a set of temperature measurements using the temperature sensor during the urination or defecation event; and generating a temperature profile associated with the urination or defecation event.

DETAILED DESCRIPTION

Figure 1:
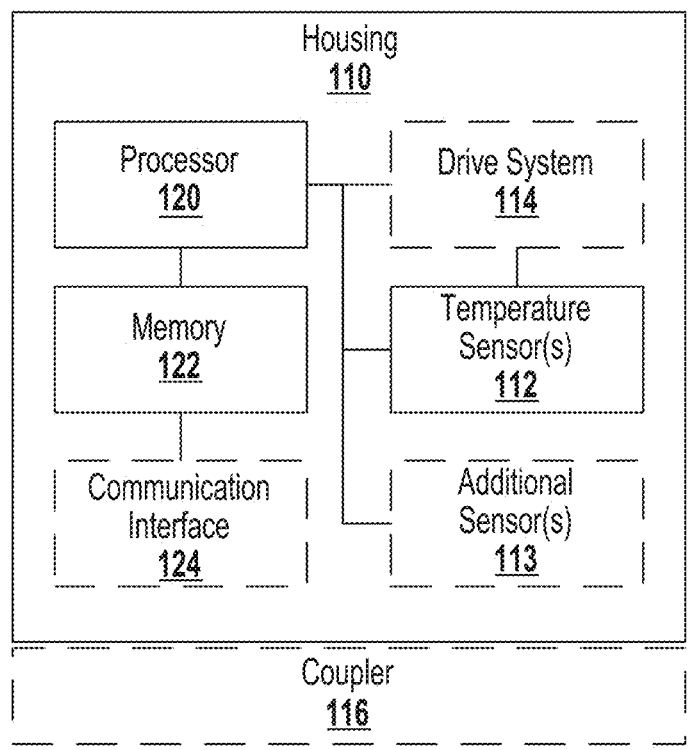
FIG. 1 is a schematic illustration of a sensing device for measuring body temperature of a subject, according to an embodiment.

The embodiments described herein relate generally to health monitoring systems and devices, and more particularly to systems, devices, and methods for monitoring signals such as temperature of urine or feces exiting a person, e.g., sitting on or standing in front of an excretion collection device or waste receptacle such as, for example, a toilet. In some embodiments, systems, devices, and methods described herein can measure an internal body temperature or core body temperature associated with an individual, which can be used to monitor certain physiological data or conditions of the individual and to inform the individual and/or healthcare providers of changes in such data or conditions necessitating certain therapies, treatments, lifestyle changes, etc.

Most individuals use toilets, urinals, or other defecation or urination devices on a daily basis. Accordingly, health monitoring that can be conducted while an individual is defecating and/or urinating into such devices can provide an unobtrusive way of regularly monitoring information about that individual. Measures such as internal body temperature or core body temperature can be useful for monitoring certain conditions of the individual, such as, for example, fever, menstrual health, circadian rhythm, insomnia and sleep disturbances, hyperthermia, hypothermia and overall health and wellbeing of the individual.

A subject's core body temperature represents a temperature of the subject's vital organs (e.g., brain or heart). Non-invasive measurements of core body temperature can be difficult. As such, many existing systems rely on measurements of external body temperature. Such systems, however, provide imprecise measurements of body temperature, as external body temperature in different regions of the body, e.g., of the skin, armpit, oral temperature or that of the inner ear, can vary. Rectal or vaginal temperature is generally considered to provide an accurate assessment of core body temperature, particularly in hypothermia, but can be a more invasive or tedious measurement method. The urinary bladder is also recognized as a site that has a temperature close to core body temperature. As such, measurements of objects that exit from the rectum and/or bladder, such as feces or urine, can therefore provide a more accurate measure of core body temperature. However, measurements of such objects need to be conducted quickly upon an object's exit from the body such that the object does not lose heat due to environmental conditions. Systems, devices, and methods described herein are designed to non-invasively measure the temperature of urine and/or feces, shortly after it exits the body, to obtain an accurate measure for core body temperature.

As described above, core body temperature can be used to monitor and assess a number of conditions associated with an individual, including, for example, fever, hyperthermia, hypothermia, and overall health and wellbeing. In some embodiments, systems, devices, and methods described herein can be used with other sensing systems and/or devices. Complementing temperature data with information from additional sensors integrated with a toilet, urinal, etc. can provide more comprehensive assessments of an individual's health. For example, other measurements as associated with an individual's health can be used to monitor and assess conditions including, for example, an individual's respiration, body weight, ballistocardiogram (BCG), pulse wave velocity (PWV), stroke output, cardiac output, weight of or urination or defecation and/or a weight change associated therewith, etc. Suitable examples of other sensing devices are described in U.S. Pat. No. 10,292,658, titled "Apparatus, System, and Method for Mechanical Analysis of Seated Individual," and issued May 21, 2019 ("the '658 patent"); International Patent Application Number PCT/US2022/024236 entitled, "Systems, Devices, and Methods for Monitoring Loads and Forces on a Seat," filed Apr. 11, 2022 ("the '236 application"); and International Patent Application Number PCT/US2022/28787 entitled, "Systems Devices, and Methods for Measuring Loads and Forces of a Seated Subject Using Scale Devices," filed May 11, 2022 ("the '787 application"). The disclosures of each of the foregoing applications are incorporated herein by reference in their entirety.

FIG. 1 is a schematic illustration of a sensing device 100, according to some embodiments. The sensing device 100 can be configured to measure temperatures of a urine stream or feces excreted by a subject, e.g., in a toilet bowl, a urinal, or other excretion collection device. In some embodiments, the subject may be sitting on a toilet seat for urinating/defecating or may be standing in front of a toilet for urinating. The sensing device 100 includes a housing 110 that houses and/or supports a processor 120, a memory 122, and one or more temperature sensor(s) 112, and optionally houses and/or supports one or more additional sensor(s) 113, a drive system 114, and/or a communication interface 124. The sensing device 100 can also include an optional coupler 116 that couples the housing 110 to a toilet or other excretion collection device. For example, the sensing device 100 can be an attachment that is coupled via the coupler 116 to a toilet or other excretion collection device. Alternatively, in some embodiments, the sensing device 100 can be integrated into a toilet and therefore not include a coupler 116.

The housing 110 can define one or more areas for accommodating (e.g., housing, containing, supporting, etc.) one or more components of the temperature assembly, including the temperature sensor(s) 112, drive system 114, processor 120, memory 122, additional sensor(s) 113 and communication interface 124. The housing 110 can be sufficiently small such that the sensing device 110 can fit within a toilet bowl (or other excretion collection device) without interfering with an individual's use of the toilet (or other excretion collection device). For example, the housing 110 can be sufficiently small to fit within a toilet bowl without blocking or obscuring the area where an individual may urinate or defecate into the toilet bowl. In some embodiments, the housing 110 can be configured to protect one or more other components of the sensing device 110, such as, for example, the processor 120, memory 122, communication interface 124, drive system 114, temperature sensor(s) 112, and/or additional sensor(s) 113. For example, the housing 110 can include compartments that are fluidically sealed, e.g., such that water, urine, or other liquids cannot enter into such compartments to damage component(s) within those compartments. In some embodiments, the housing 110 can include protrusions, ledges, recesses, etc. that can prevent accidental forces being applied to (or reduce accidental forces being applied to) one or more of the processor 120, memory 122, communication interface 124, drive system 114, temperature sensor(s) 112, and/or additional sensor(s) 113. In some embodiments, the housing 110 can be formed of a rigid material, while in other embodiments, the housing 110 can be formed of a flexible material.

The temperature sensor(s) 112 can be configured to measure the temperature of a urine stream and/or feces as it is excreted from the subject's body. The temperature sensor(s) 112 may either be static or movable, e.g., in a linear motion and/or rotationally about an axis to span the opening of the toilet bowl (or other excretion collection device) through which urine and/or feces may be collected. As such, the temperature sensor(s) 112 can be used to capture a temperature of urine and/or feces regardless of the exact location where such urine and/or feces is received into the toilet bowl (or other excretion collection device). In particular, depending on the position that an individual is seated on a toilet or standing around a toilet, the individual may excrete urine and/or feces into a different location of the toilet bowl. Therefore, by having temperature sensor(s) 112 (e.g., an array of temperature sensors) that span an entire region of the toilet bowl or a movable sensor that can move to cover an entire region of the toilet bowl, the sensing device 100 can be configured to measure an individual's urine and/or feces independent of the location where the urine and/or feces is discharged into the toilet bowl. In an embodiment, the temperature sensor(s) 112 can include a non-contact infrared (IR) thermometer or temperature sensor, which can measure temperature based on the thermal radiation or black-body radiation emitted by the object being measured. The non-contact infrared temperature sensor can include a lens that focuses the infrared thermal radiation emitted by an object onto a detector, which converts the radiant power to an electrical signal representative of the temperature of the object. Examples of non-contact infrared thermometers include infrared thermopile sensors, diode-based digital infrared sensors, and thermal imaging cameras. Alternatively or additionally, the temperature sensor(s) 112 can include a thermopile infrared array with multiple pixels. When using a thermopile infrared array, there may be no need to scan or move the sensor to record the temperature profile of the object.

In some embodiments, an optional coupler 116 may be used to couple the housing 110 to a toilet or other excretion collection device, e.g., to secure the housing 110 firmly in place. In some embodiments, the coupler 116 can include a mechanical coupler, such as, for example a latch, a clamp, a hook, a fastener, or other mechanical component for securing the sensing device 100 to a portion of the toilet or other excretion collection device. In some embodiments, the coupler 116 can include an adhesive, magnet(s), and/or electrically activated component(s) for securing the sensing device 110 to a portion of the toilet or other excretion collection device.

In some embodiments, an optional drive system 114 may be used to control the position and/or orientation of one or more temperature sensor(s) 112. For example, the drive system 114 can be configured to linearly translate and/or rotate one or more temperature sensor(s) 112, e.g., to enable the temperature sensor(s) 112 to collect temperature data at multiple positions or viewing angles. In some embodiments, the drive system 114 can be configured to move one or more temperature sensor(s) 112 such that the viewing range of the temperature sensor(s) 112 encompasses or covers at least a substantial majority of a length of the toilet bowl (or other excretion collection device). In particular, a temperature sensor 112 may have a field of view (FOV) that does not cover an entire length of a toilet bowl (or other excretion collection device). As such, the temperature sensor 112 if used in isolation and without any movement, may not capture the temperature of urine and/or feces being deposited into certain locations of the toilet bowl (or other excretion collection device). The sensing device 100 as described herein can therefore include a drive system 114 that is configured to move the temperature sensor 112 (or multiple temperature sensors 112) to collect measurements across an entire length and/or area (or at least a substantial majority of the length and/or area) of the toilet bowl. In some embodiments, the drive system 114 can include a single motor that rotates one or more temperature sensor(s) 112 through a series of viewing angles. Alternatively, the drive system 114 can include multiple motors that can translate the temperature sensor(s) 112 along multiple axes and/or rotate the temperature sensor(s) 112 about multiple axes. In some embodiments, the sensing device 100 may not include a drive system 114. In such embodiments, the sensing device 110 may have a temperature sensor 112 or an array of temperature sensors 112 that span or cover an entire length and/or area (or at least a substantial majority of the length and/or area) of a toilet bowl (or other excretion collection device) and therefore a drive system 114 may not be necessary for the operation of the device 100. In some embodiments, the sensing device 110 may include a single temperature sensor 112, e.g., that can be rotated or translated to span the area for receiving a subject's urine and/or feces. Alternatively, the sensing device 110 can include 2 sensors, 3 sensors, 4, sensors, 5 sensors, about 10 sensors, about 15 sensors, about 20 sensors, about 25 sensors, about 50 sensors, about 75 sensors, about 100 sensors, or any other values or ranges therebetween.

In some embodiments, the sensing device 100 can include optional additional sensor(s) 113 that can collect additional data of the subject, e.g., while the subject is seated on the toilet seat and/or standing in front of the toilet seat. For example, the sensing device 110 can include force sensor(s), impedance sensor(s), pulse oximeter(s), skin temperature sensor(s), and/or other types of sensors. The additional sensor(s) 113 can be supported and/or housed by the housing 110. For example, in an embodiment, the housing 110 can be implemented as a toilet ring and/or an attachment to a toilet ring, and the temperature sensor(s) 112 and/or additional sensor(s) 113 can be positioned at different locations about the toilet ring. In some embodiments, multiple temperature sensor(s) 112 can be used (alone or in combination with additional sensor(s)) to measure the temperature of urine and/or feces, and the temperature data from the multiple sensors can be averaged, e.g., to reduce noise (e.g., by averaging or comparing the independent signals) and/or provide a more accurate measure of core body temperature and/or other physiological characteristics or conditions. In some embodiments, the additional sensor(s) 113 can include motion, light, force, or other types of sensors for detecting when an individual is using the toilet or other excretion collection device. For example, such a sensor 113 can detect movement near an opening of the toilet or other excretion collection device and/or pressure or forces on a seat of the toilet or other excretion collection device. The sensor 113 can then send this information to a processor (e.g., processor 120 as described below), and the processor can be configured to activate the temperature sensor(s) 112 and/or drive system 114 to capture the temperature of the urine and/or feces deposited in the toilet or other excretion collection device by the individual.

The data collected by the temperature sensor(s) 112 and/or additional sensor(s) 113 can be received at the processor 120. In some embodiments, the processor 120 can be configured to process (e.g., filter, average, etc.) the data collected by the temperature sensor(s) 112 and/or additional sensor(s) 113. In some embodiments, the processor 120 can be configured to analyze the data collected by the temperature sensor(s) 112 and/or additional sensor(s) 113, e.g., to monitor and/or evaluate various physiological data or conditions of the subject. The processor 120 can be any suitable processing device configured to run and/or execute functions associated with processing and/or analyzing sensor data from temperature sensor(s) 112 and/or additional sensor(s) 113. For example, the processor 120 can be configured to process and/or analyze sensor data (e.g., received from sensor(s) 112 and/or 113) to determine a temperature, weight, BCG, ECG, posture, impedance, or other physiological data or conditions of an individual. Additionally or alternatively, the processor 120 can cause the drive system 114 to modify the angle or position of the sensor(s) 112 and/or 113 with respect to a toilet or other excretion collection device. For example, the processor 120 can be configured to control the drive system 114 to move the sensor(s) 112 and/or 113 according to a predetermined algorithm. In some embodiments, the processor 120 can be configured to send the data collected by the temperature sensor(s) 112 and/or additional sensor(s) 113 to other devices (e.g., remote compute devices or a user device) such that those devices can process and/or analyze the data. The processor 120 can be coupled to an optional communication interface 124, which can be used to send information to and/or receive information from other devices. The processor 120 can be a general purpose processor, a Field Programmable Gate Array (FPGA), an Application Specific Integrated Circuit (ASIC), a Digital Signal Processor (DSP), and/or the like.

The processor 120 can be operatively coupled to the memory 122. The memory 122 can be, for example, a random access memory (RAM), a memory buffer, a hard drive, a database, an erasable programmable read-only memory (EPROM), an electrically erasable read-only memory (EEPROM), a read-only memory (ROM), and/or so forth. In some embodiments, the memory 122 stores instructions that cause processor 120 to execute modules, processes, and/or functions associated with processing and/or analyzing sensor data from sensor(s) 112 and/or 113, controlling drive system 114, or sending sensor data to other devices via communications interface 124.

Figure 2:
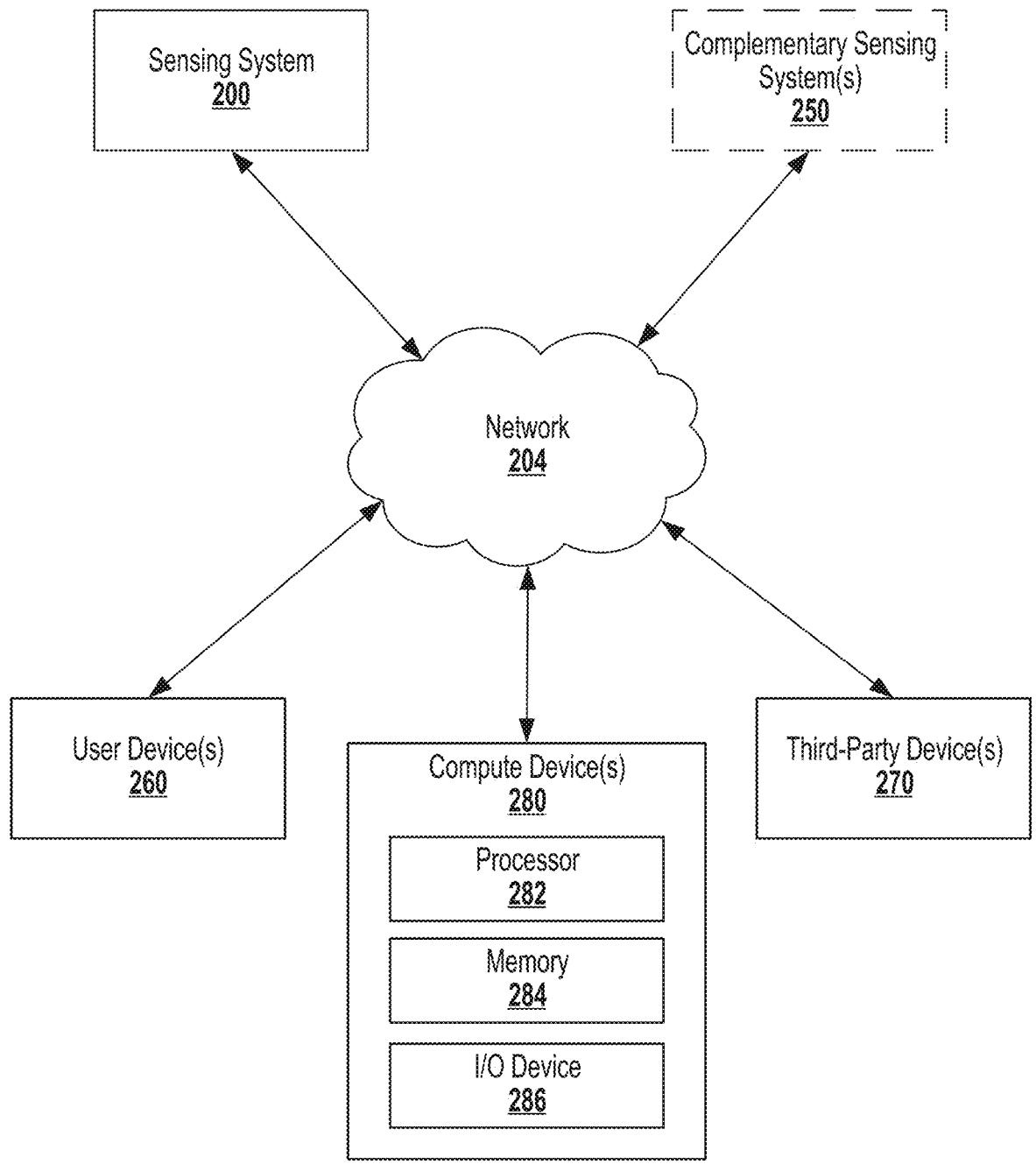
FIG. 2 schematically depicts a network of devices for monitoring physiological conditions of a subject, according to an embodiment.

FIG. 2 depicts a block diagram illustrating a sensing system 200 in communication with other devices via a network 204. In some embodiments, sensing system 200 can be configured to measure physiological data or signals associated with an individual seated on a toilet, including, for example, a core body temperature of the individual. Sensing system 200 can include component(s) that are structurally and/or functionally similar to those of other sensing systems and devices described herein, including, for example, the sensing device 100. For example, sensing system 200 can include one or more sensor(s) that can be configured to measure temperature. The sensor(s) can be functionally and/or structurally similar to sensor(s) 112. The sensor(s) can be disposed within a sensing device (e.g., sensing device 100) and configured to collect sensor data representative of the temperature of a urine stream and/or feces as they are excreted from the body of a subject seated on or standing in front of a toilet, urinal, or other excretion collection device. The temperature measured by the sensor(s) can be used (e.g., by a processor, such as, for example, processor 120) to determine an internal body temperature or core body temperature of the subject.

In some embodiments, the sensing system 200 can optionally communicate with a complementary sensing system(s) 250 via a network 204. The complementary sensing system(s) 250 can be configured to measure physiological data or signals associated with the same individual as the sensing system 200. For example, an individual can be urinating or defecating into a toilet or other excretion collection device, and the sensing system 200 can measure a temperature of the urine stream or feces as it is excreted from the body and the complementary sensing system 250 can measure other data associated with the individual (e.g., loads or forces, skin temperature, impedance, etc.). In some embodiments, the sensing system 200 and the complementary sensing system 250 can be collectively configured to measure data associated with the individual, which can be used to evaluate one or more physiological conditions of the individual.

While not depicted, the complementary sensing system(s) 250 can include one or more sensors, communication interfaces, and/or processors for measuring and/or processing data associated with an individual using toilet or other excretion collection device. In some embodiments, the complementary sensing system 250 can be configured to receive data (e.g., temperature data) from the sensing system 200, and an onboard processor of the complementary sensing system 250 can be configured to process and/or analyze this data in combination with other data collected by the complementary sensing system 250 to determine information such as weight, BCG, impedance, or other physiological data or conditions of a subject (e.g., an individual seated on a toilet). In some embodiments, the complementary sensing system(s) 250 can include a sensing system that is integrated into a toilet seat, as described in the '658 patent and '236 application, which have been incorporated by reference above.

In some embodiments, the sensing system 200 can be configured to communicate with other devices, such as a compute device 280, one or more user device(s) 260, one or more third-party device(s) 270, etc., via the network 204. The network 204 can include one or more network(s) that may be any type of network (e.g., a local area network (LAN), a wide area network (WAN), a virtual network, a telecommunications network) implemented as a wired network and/or wireless network and used to operatively couple to any compute device, including sensing system 200, complementary sensing system(s) 250, compute device 280, user device(s) 260, and third-party device(s) 270.

Optionally, the sensing system 200 can be configured to send data measured by sensor(s) via a communication interface (e.g., communication interface 124) to the complementary sensing system(s) 250, the compute device 280, one or more user device(s) 260, and/or one or more third-party device(s) 270. In some embodiments, the sensing system 200 can include onboard processing, such as, for example, a processor implemented as a microprocessor (e.g., processor 120), to process sensor data (e.g., filter, convert, average, etc.) prior to sending the sensor data to the complementary sensing system(s) 250, compute device 280, one or more user device(s) 260, and/or one or more third-party device(s) 270. Alternatively, sensing system 200 can be configured to send raw sensor data to the complementary sensing system(s) 250, the compute device 280, one or more user device(s) 260, and/or one or more third-party device(s) 270. In some embodiments, the processor can be configured to analyze the sensor data and/or determine information such as core body temperature or other physiological data or conditions of a subject (e.g., an individual seated on a toilet). In some embodiments, the processor can be configured to present this information to a user, e.g., via an onboard display, audio device, or other output device. In some embodiments, the processor can interface with the communication interface to transmit information to another device (e.g., complementary sensing system 250, user device 260, compute device 280, or third-party device 270) for presenting information to a user. The communication interface can be configured to allow two-way communication with an external device, including, for example, the compute device 280, one or more user device(s) 260, and/or one or more third-party device(s) 270. The communication interface can include a wired or wireless interface for communicating over the network 204.

The compute device 280 can be configured to process and/or analyze the sensor data, e.g., received from the sensor(s). In some embodiments, the compute device 280 can be a nearby compute device (e.g., a local computer, laptop, mobile device, tablet, etc.) that includes software and/or hardware for receiving the sensor data and processing and/or analyzing the sensor data. In some embodiments, the compute device 280 can be a server that is remote from the sensing system 200 but can communicate with the sensing system 200 via network 204 and/or via another device on the network 204 (e.g., a user device 260). For example, sensing system 200 can be configured to transmit sensor data to a nearby device (e.g., a complementary sensing system 250 or a user device 260), e.g., via a wireless network (e.g., Wi-Fi, Bluetooth®, Bluetooth® low energy, Zigbee and the like), and then that device can be configured to transmit the sensor data to the compute device 280 for further processing and/or analysis.

The user device(s) 260 can be compute device(s) that are associated with a user of a toilet or other excretion collection device equipped with the sensing system 200. Examples of user device(s) 260 can include a mobile phone or other portable device, a tablet, a laptop, a personal computer, a smart device, etc.). In some embodiments, a user device 260 can receive sensor data from the sensing system 200 and process that sensor data before passing the sensor data to the compute device 250. For example, a user device 260 can be configured to reduce noise (e.g., filter, time average, etc.) raw sensor data. In some embodiments, a user device 260 can be configured to analyze the sensor data and present (e.g., via a display) information representative of or summarizing the sensor data. In some embodiments, a user device 260 can provide weight information, body temperature information, heart rate information, etc. to a user. In some embodiments, a user device 260 can transmit the sensor data to the compute device 260, which can analyze the sensor data and send information representative of or summarizing the sensor data back to the user device 260 for presenting (e.g., via a display) to a user.

The third-party device(s) 270 can be compute device(s) associated with other individuals or entities that have requested and/or been provided access to a user's data. For example, the third-party device(s) 270 can be associated with healthcare professionals (e.g., physicians, nurses, therapists) and/or caregivers of the user. The user can select to have certain third parties have access to the user's health data (e.g., including health data obtained from sensor data collected by sensing system 200). The third parties can then track the user's health information to determine whether the user is at risk for certain conditions and/or needs certain interventions, treatments, or care.

The compute device 280 can include a processor 282, a memory 284, and an input/out device (I/O) 286 (or a multiplicity of such components). The memory 284 can be, for example, a random access memory (RAM), a memory buffer, a hard drive, a database, an erasable programmable read-only memory (EPROM), an electrically erasable read-only memory (EEPROM), a read-only memory (ROM), and/or so forth. In some embodiments, the memory stores instructions that cause the processor to execute modules, processes, and/or functions associated with processing and/or analyzing sensor data from sensing system 200.

The processor 282 of compute device 280 can be any suitable processing device configured to run and/or execute functions associated with processing and/or analyzing sensor data from sensing system 200. For example, the processor 282 can be configured to process and/or analyze sensor data (e.g., received from the sensor(s) of the sensing system 200, such as, for example, sensor(s) 112 and/or 113), to determine a core body temperature, weight, BCG, ECG, posture, impedance, or other physiological data or conditions of an individual. The processor 282 can be a general purpose processor, a Field Programmable Gate Array (FPGA), an Application Specific Integrated Circuit (ASIC), a Digital Signal Processor (DSP), and/or the like.

In some embodiments, the compute device 280 includes an I/O device 286 which in turn can include one or more components (e.g., a communication or network interface) for receiving information and/or sending information to other devices (e.g., sensing system 200, user device(s) 260, third-party device(s) 270). In some embodiments, the I/O device 286 can optionally include or be operatively coupled to a display, audio device, or other output device for presenting information to a user. In some embodiments, the I/O device 286 can optionally include or be operatively coupled to a touchscreen, a keyboard, or other input device or receiving information from a user.

While complementary sensing system(s) 250, user device(s) 260, and third-party-device(s) 270 are not depicted with any onboard memory, processing, and/or I/O devices, it can be appreciated that any one of these devices can include components (e.g., a memory, a processor, a I/O device, etc.) that enable it to perform functions such as, for example, processing and/or analyzing the sensor data, or using the sensor data to determine physiological information about an individual (e.g., core body temperature, weight, BCG, posture, impedance, etc.).

Figure 3A:
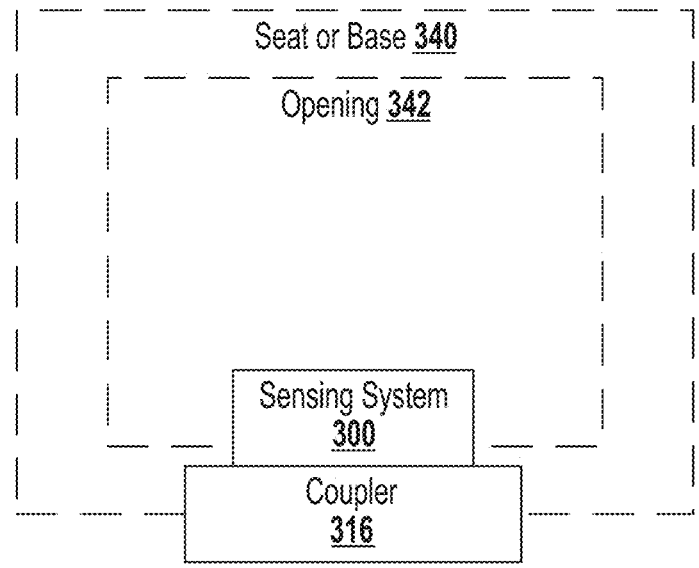
FIG. 3A is a schematic illustration of a temperature sensing device arranged with respect to a seat or base of a defection and/or urination device, according to an embodiment.

FIG. 3A is a schematic illustration of a temperature sensing system 300 coupled to a seat or base 340 of a toilet or other excretion collection device via a coupler 316, according to an embodiment. The sensing system 300 can be structurally and/or functionally similar to other sensing systems and devices described herein, including, for example, sensing device 100 and/or sensing system 200, and can include components that are structurally and/or functionally similar to such systems and devices. For example, the coupler 316 can be structurally and/or functionally similar to the coupler 116, as described with reference to FIG. 1. The sensing system 300 can also include temperature sensor(s) (e.g., temperature sensor(s) 112), e.g., for measuring a temperature of urine and/or feces received in the seat or base 340 of the toilet or other excretion collection device. The coupler 316 can be configured to removably couple the sensing system 300 to the seat or base 340. The sensing system 300, when coupled to the seat or base 340 via the coupler 316, can be positioned such that the temperature sensor(s) of the sensing system 300 can scan at least a substantial portion of the opening 342 of the toilet or other excretion collection device to measure the temperature of the urine and/or feces received therein. In some embodiments, the sensing system 300 can also include additional sensor(s) (e.g., additional sensor(s) 113) for detecting when an individual is using the toilet or other excretion collection device and/or for measuring other physiological parameters of an individual. For example, the sensing system 300 can include a motion or light sensor that can detect when there is movement near the opening 342 of the seat or base 340. In such cases, the motion or light sensor can send a signal to a processor (e.g., an onboard processor such as processor 120), and the processor can be configured to activate the temperature sensor(s) in response to receiving the signal.

Figure 3B:
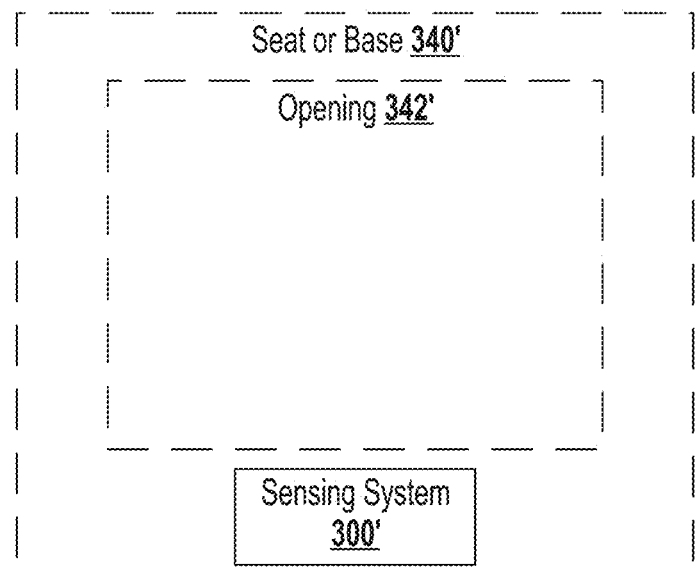
FIG. 3B is another schematic illustration of a temperature sensing device arranged with respect to a seat or base of an excretion collection device, according to an embodiment

FIG. 3B depicts another schematic illustration of a temperature sensing system 300' integrated directly into the seat or base 340' of a toilet or other excretion collection device, according to an embodiment. The sensing system 300' can be structurally and/or functionally similar to sensing system 300 (and other sensing systems and/or devices described herein) but be integrated into the seat or base 340' instead of being coupled via a coupler 316. As integrated, the sensing system 300' is positioned such that its temperature sensor(s) (e.g., temperature sensor(s) 112) can scan at least a substantial portion of the opening 342' of the toilet or other excretion collection device to measure the temperature of urine and/or feces received into the opening 342'.

Figure 4:
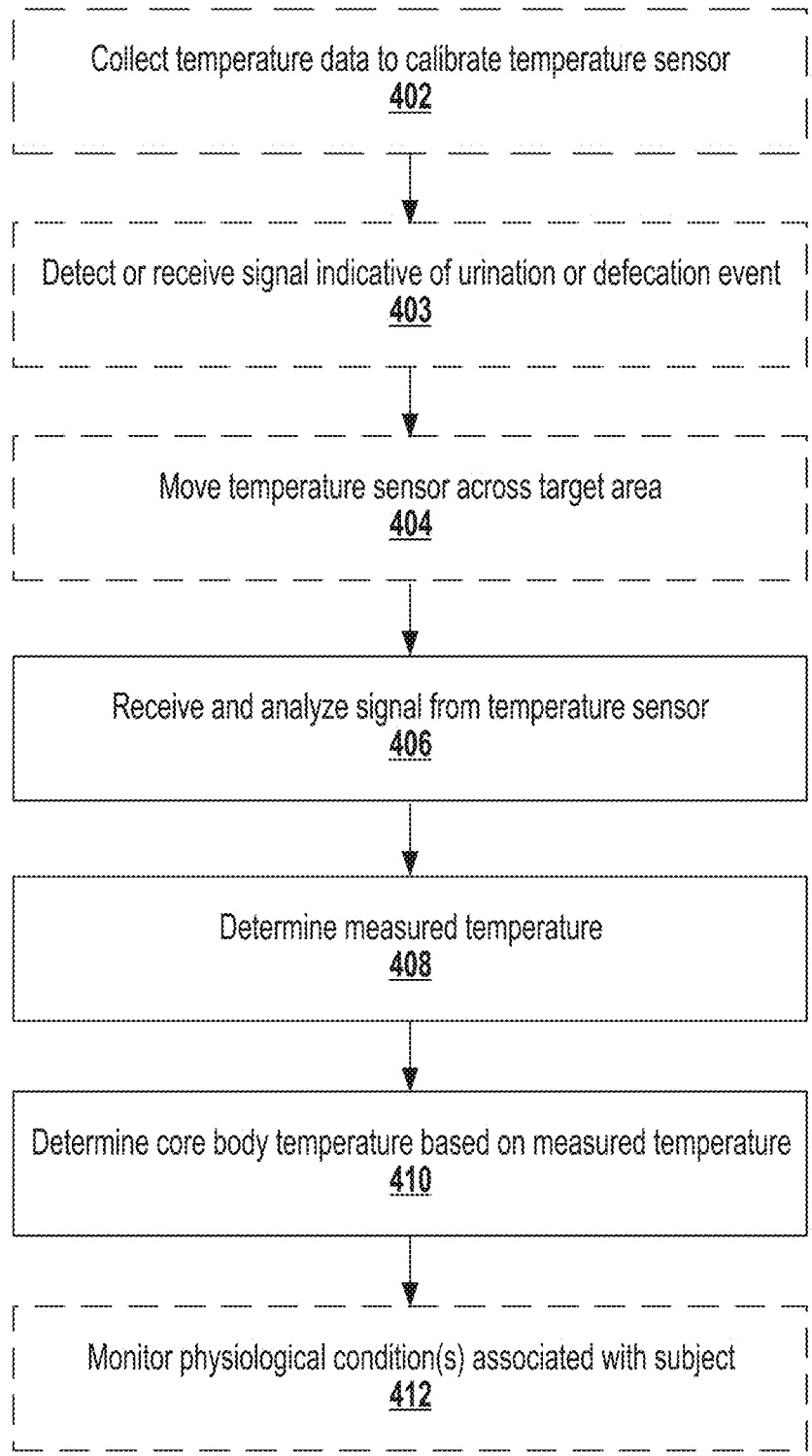
FIG. 4 is a flow chart of an example method of operating a sensing device that measures temperature data associated with a subject via characterization of the subject's urine and/or feces, according to an embodiment.

FIG. 4 depicts an example method 400 of the operation of systems and devices described herein. Systems and devices described herein, such as, for example, sensing device 100 and/or systems 200, 300, 300', can include one or more temperature sensor(s) (e.g., temperature sensors(s) 112) for measuring a temperature of urine and/or feces that are received in a toilet or other excretion collection device. The systems or devices can be installed on the toilet or other excretion collection device such that its temperature sensor(s) can scan at least a substantial portion of an opening of the toilet or other excretion collection device that receives the urine and/or feces.

The temperature sensor(s) of the sensing system installed onto a toilet or other excretion collection device can be calibrated, at 402. For example, the temperature sensor(s) can collect data of reference source(s) (e.g., blackbody source(s) with known temperature and/or surface characteristics (e.g., emissivity)) and send that data to a processor (e.g., onboard processor (e.g., processor 120) and/or processor associated with an external compute device (e.g., user device 260, compute device 280)), and the processor can calibrate the temperature sensor(s) based on the sensor data and the known temperature and/or surface characteristics of the reference source(s). In some instances, the temperature sensor(s) can be calibrated to have a predefined accuracy. For example, the temperature sensor(s) can be calibrated to have an accuracy of about 0.05° C., 0.1° C., about 0.2° C., about 0.3° C., about 0.4° C., about 0.5° C., or about 1° C., including all ranges and values therebetween (e.g., greater than about 0.05° C., less than 1° C., or between about 0.05° C. and about 1° C.). The temperature sensor(s) can be calibrated to have a predefined accuracy within a predefined range of temperatures, e.g., of between about 20° C. to about 40° C., including other subranges therebetween. For example, the temperature sensor(s) can be calibrated to have a predefined accuracy within the range of between about 30° C. to about 40° C. In some embodiments, the temperature sensor(s) can be factory calibrated or calibrated prior to being installed by an individual on their toilet or other excretion collection device. In some embodiments, the temperature sensor(s) can be calibrated during or after installation of the system on a toilet or other excretion collection device, e.g., to account for different attachments of the system components to the toilet or other excretion collection device and/or other environmental factors (e.g., typical lighting, ambient room temperature, etc.).

In an example calibration procedure, a temperature sensor (e.g., 112) such as an IR sensor can be calibrated with a blackbody source that has known temperature and surface characteristics. An example of a surface characteristic is emissivity, which shows how well an object can emit electromagnetic radiation. Emissivity ranges from 1 for an ideal blackbody to 0. Emissivity of 1 is an indicator of a perfect emitter, but in practical applications, blackbodies are not 100% efficient. For example, a blackbody used to calibrate an IR sensor such as the MLX90614ESF-DCI sensor can have an emissivity of 0.97 with temperature accuracy of ±0.3° C. in a predefined range of temperatures (e.g., 22-40° C.). It can be desirable to increase the accuracy of the sensor in a narrower range, e.g., in the range of 30-40° C. before using the sensor to perform measurements. To calibrate the IR sensor in this narrower range, in an exemplary embodiment, the IR sensor can be placed to point toward an active temperature-controlled surface of a blackbody source at a distance of 5 cm. During the calibration process, the temperature of the blackbody can be changed from 30 to 40° C. with intervals of 1° C. The temperature of black body can then be measured using the IR sensor after each interval change, with a wait time of 5 minutes between doing the measurement for each interval, e.g., to make sure the blackbody temperature is stabilized before the measurement. Multiple measurements (e.g., approximately 65) can be performed at each temperature and the median value can be selected for calibrating the sensor.

The factory calibration of the sensor is done under the assumption that the object that it is facing toward has an emissivity of 1. The error introduced by the difference between sensor factory calibration based on emissivity 1 and an actual blackbody emissivity can be calculated based on the following equation:

$$\delta_E = T_b - \sqrt[4]{\frac{\varepsilon_0}{\varepsilon_b}(T_b^4 - T_a^4) + T_a^4}$$

Where $\delta_E$, $T_b$, $\varepsilon_b$, $\varepsilon_b$, and $T_a$ are the emissivity error, black body temperature, sensor original set emissivity, black body emissivity, and ambient temperature respectively.

Table 1 summarizes the results of calibration for an example sensor. The sensor error is the absolute error after compensating for the error originating from the emissivity mismatch between blackbody and the sensor. In Table 1, the blackbody temperature is equal to the measured temperature adjusted by the emissivity error and the sensor error.

TABLE 1

| Measured temperature | Measured ambient temperature | Blackbody temperature | Blackbody temperature + Emissivity error | Sensor error | Error after calibration |
|---|---|---|---|---|---|
| 29.8 | 23.1 | 30.0 | 29.8 | 0.0 | 0.04 |
| 34.1 | 23.8 | 35.0 | 34.7 | 0.6 | −0.07 |
| 34.9 | 23.9 | 36.0 | 35.7 | 0.8 | −0.02 |
| 35.7 | 23.9 | 37.0 | 36.6 | 0.9 | −0.02 |
| 36.5 | 24.0 | 38.0 | 37.6 | 1.1 | 0.05 |

TABLE 1-continued

| Measured temperature | Measured ambient temperature | Blackbody temperature | Blackbody temperature + Emissivity error | Sensor error | Error after calibration |
|---|---|---|---|---|---|
| 37.4 | 24.1 | 39.0 | 38.6 | 1.2 | 0.01 |
| 38.2 | 24.3 | 40.0 | 39.6 | 1.4 | 0.02 |

After collecting the sensor data, a calibration was done by applying a linear fit to the sensor output to minimize a difference between the measured temperature and the blackbody temperature adjusted with emissivity error. The calibration curve slope and intercept can be expressed as follows: Calibrated Measured Temperature=1.15×Measured temperature−4.65+Emissivity error Referring back to FIG. 4, the sensing system can optionally receive signals, e.g., data from one or more motion, force, or optical sensors for detecting use of an excretion collection device by an individual, at 403. The sensing system can have or be coupled to a processor (e.g., onboard processor (e.g., processor 120) and/or processor associated with an external compute device (e.g., user device 260, compute device 280)) that receives signals captured by one or more sensor(s) of the sensing system and can determine that a urination or defecation event is about to occur or is occurring. The signals can be received when a user is seated on the toilet or other excretion collection device or standing in front of the toilet or other excretion collection device, such that the signals can be indicative of the urination or defecation event.

Based on the signals received by the sensing system at 403, the processor can activate the temperature sensor(s) of the sensing system to begin measuring a temperature of an object (e.g., urine and/or feces) being received into the toilet or other excretion collection device. Optionally, the processor can control the drive system (e.g., drive system 114) to move one or more temperature sensor(s) of the sensing system across a target area, at 404. The temperature sensor(s), when moved, can scan at least a substantial portion of an opening of the toilet bowl or other excretion collection device, and can measure a temperature of urine and/or feces being received into the bowl or other excretion collection device. Alternatively, an array of temperature sensors can be positioned around at least a portion of the opening of the toilet or other excretion collection device, and can be activated together to capture the temperature of urine and/or feces being received into the toilet or other excretion collection device. The array of temperature sensors can be arranged in a row along a side of the toilet or other excretion collection device (e.g., a frontside or a backside), and can have field of views that together span at least a substantial portion of the opening of the toilet or other excretion collection device. As described above, the sensing system can include a single sensor (or a smaller number of sensors) that is rotated or translated to span the area for receiving the urine and/or feces, or a plurality of sensors (e.g., between 2 and about 100 sensors) that together span the area for receiving the urine and/or feces.

The processor can receive and/or analyze the signal(s) from the temperature sensor(s), at 406, and determine the measured temperature of the urine and/or feces of the individual, at 408. Since the urine and/or feces being received into a toilet, urinal, or other excretion collection device may not span an entire area of the excretion collection device, the temperature data collected by the temperature sensor(s) may be in the form of a temperature profile. The temperature profile may represent the temperature measured by the temperature sensor(s) across different angular positions (e.g., viewing angles) or spatial positions. As described above, the temperature sensor(s) of a sensing device can be rotated and/or translated to capture temperature data across an entire length and/or area (or a substantial range of the entire length and/or area) of the opening of the toilet, urinal, or other excretion collection device, or an array of sensors can be used to capture such temperature data. As such, the temperature sensors can measure temperature data at different angular and/or spatial positions, and the temperature data can be combined together into a temperature profile that is indicative of the temperature distribution across the entire length and/or area of the opening for receiving the urine and/or feces. These temperature profiles can be analyzed and used to determine the temperature of the urine and/or feces. Further details of determining the measured temperature of the urine and/or feces is provided with reference to FIGS. 5 and 6.

The processor can use the measured temperature of the urine and/or feces to determine a core body temperature of the individual, at 410. In some embodiments, the measured temperature can be equated to the core body temperature. As described above, urine and/or feces can be accurate predictors for core body temperature when measured quickly upon exit from an individual's body. In some embodiments, the processor can be configured to estimate the core body temperature based on the measured temperature of the urine and/or feces, e.g., by applying an algorithm or model. At 412, the processor can optionally use the determined core body temperature to monitor one or more physiological condition(s) of the individual, such as, for example, fever, hyperthermia, hypothermia etc. Alternatively, the processor can predict the core body temperature based on the measured temperature of the urine and/or feces, e.g., using an algorithm such as a linear correlation, a machine learning algorithm, etc. The core body temperature can be used to monitor one or more physiological condition(s) associated with a subject (e.g., fever, menstrual health, circadian rhythm, insomnia and sleep disturbances, hyperthermia, hypothermia and overall health and wellbeing), at 412. Optionally, the processor can present information such as the core body temperature, the monitored condition(s), etc. to a user and/or provide feedback to a user based on such information, e.g., through one or more compute devices (e.g., user device 260, compute device 280, and/or third-party device 270).

While method 400 is described with reference to a processor, it can be appreciated that any processor or combination of processors described herein (e.g., onboard processor (e.g., processor 120) and/or processor associated with an external compute device (e.g., user device 260, compute device 280)) can be used to perform one of more of the steps of method 400. Such processors can be configured to send and/or receive data from each other to perform the steps of method 400.

Figure 5:
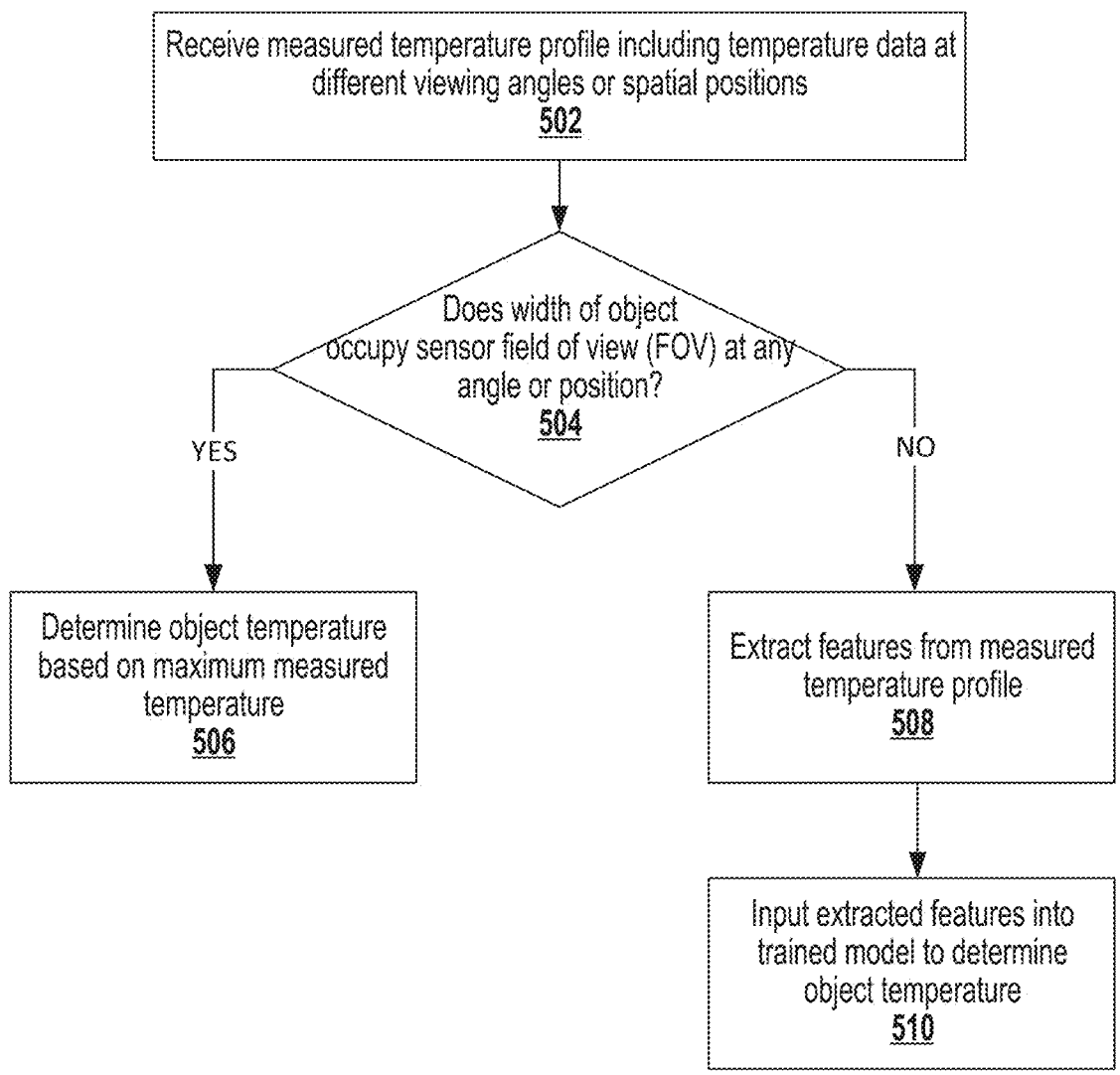
FIG. 5 is a flow chart of an example method of determining a temperature of an object (e.g., feces and/or urine) using temperature profiles measured by a sensing system, according to an embodiment.

FIG. 5 is a flow chart of an example method of determining a temperature of an object (e.g., feces and/or urine), according to embodiments. As described above with reference to FIG. 4, a processor (e.g., onboard processor (e.g., processor 120) and/or processor associated with an external compute device (e.g., user device 260, compute device 280)) can receive temperature data from one or more temperature sensor(s), at 502. The temperature data can be in the form of a temperature profile, which can represent the distribution of temperature measured by the temperature sensor(s) across a range of different viewing angles or positions.

As noted above, one or more temperature sensor(s) may be used to collect temperature data when a subject's urine and/or feces is being received into an opening of a toilet, urinal, or other excretion collection device. In some embodiments, the temperature sensor(s) may be configured to collect temperature data at different viewing angles or positions. In some embodiments, the temperature sensor(s) can be moved (e.g., translated or rotated) into different viewing angles or positions, e.g., using a drive system (e.g., drive system 114), and the temperature sensor(s) can collect temperature data at each of those viewing angles or positions. Alternatively or additionally, a plurality of temperature sensor(s) can be placed at different viewing angles or positions, and each temperature sensor can be used to collect temperature data at its different viewing angle or position. The temperature data collected by the temperature sensor(s) at the different viewing angles or positions can be combined into a temperature profile.

As described above, the temperature sensor(s) may have a fixed FOV and be configured to measure temperature by measuring a weighted average temperature of the objects in their FOV. As such, target objects that have a width smaller than the FOV of the temperature sensor can introduce error to the sensor output, e.g., due to background objects having different temperature than the target object. Generally, urine streams have a small width and therefore may not fully cover the FOV of a temperature sensor. For example, using a sensor with a FOV of 5 degrees, a urine stream with a typical width of about 8 mm when set at distances of greater than about 10 cm would have a width that is smaller than the sensor's FOV. While sensors with smaller FOVs can be used, the location of a urine stream may change, and therefore a smaller FOV sensor may not be suitable for fully capturing the temperature data of a urine stream.

Figure 7A:
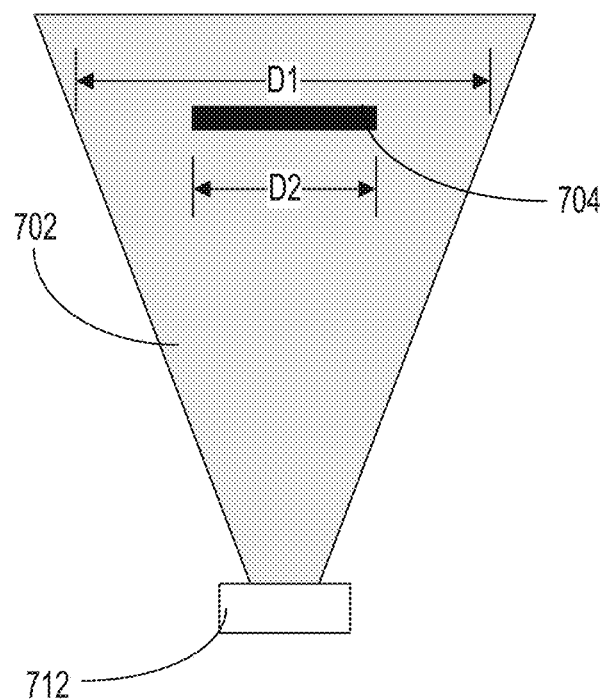
FIG. 7A shows a schematic view of an example instance of measuring a temperature profile, where a width of an object partially occupies a field of view of a temperature sensor, according to an embodiment.
Figure 7B:
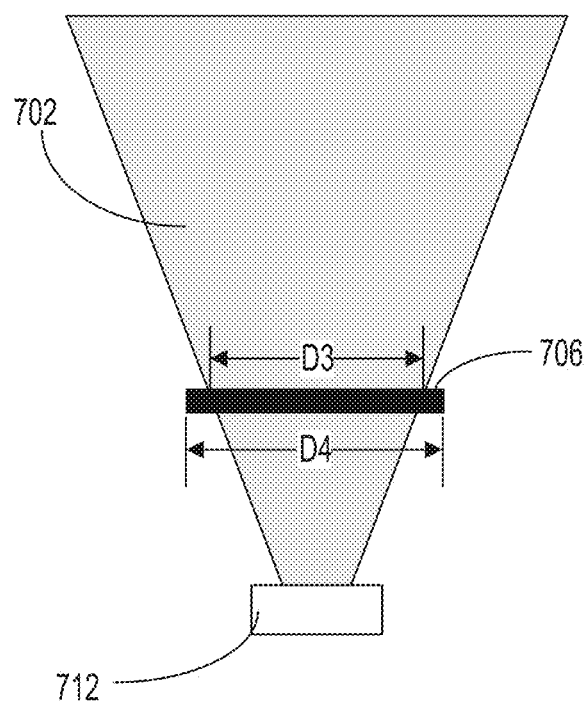
FIG. 7B shows a schematic view of an example instance of measuring a temperature profile when a width of an object completely occupies a field of view of a temperature sensor, according to an embodiment.

FIGS. 7A and 7B schematically depict objects within a FOV of a temperature sensor, according to embodiments. FIG. 7A depicts an object 704 (e.g., a urine stream and/or feces) where the width of the object partially occupies a FOV of a temperature sensor 712. The temperature sensor 712 may be part of a sensing system (e.g., sensing device 100, 200, 300, 300') that is disposed near or about an opening of a toilet or other excretion collection device. The temperature sensor 712 can have a FOV 702. The object 704 can be an object that is received within the opening of the toilet or other excretion collection device and can have a width of D2. At the distance where the object 704 is relative to the sensor 712, the width D2 of the object 704 is less than a diameter D1 of the sensor's FOV 702. In comparison, FIG. 7B depicts an object 706 that has a width D4 that occupies the FOV 702 of the sensor 712, according to some embodiments. Specifically, at the distance where the object 706 is relative to the sensor 712, the width D4 of the object 706 is at least the diameter D3 of the FOV 702 of the temperature sensor 712. Depending whether the width of an object occupies the FOV of the temperature sensor 712, the temperature measured by the temperature sensor 712 varies. For example, the temperature sensor 712 can measure temperature by determining a weighted average temperature of the objects in its FOV. As such, if a target object does not occupy the FOV of the temperature sensor 712, then the temperature sensor 712 may detect a temperature that is different than the temperature of that object.

Figure 8A:
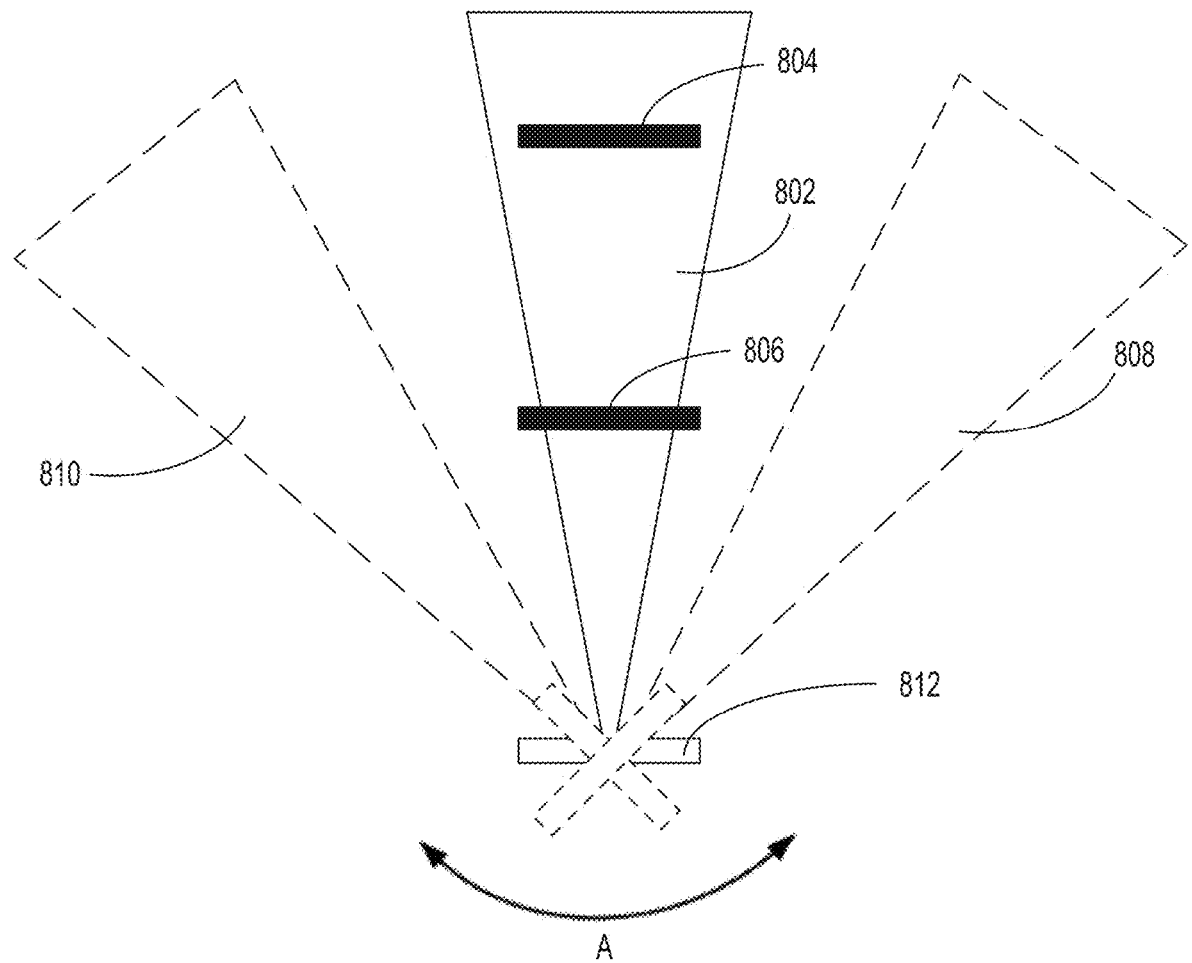
FIG. 8A shows a schematic view of an example arrangement of a temperature sensor, according to an embodiment.
Figure 8B:
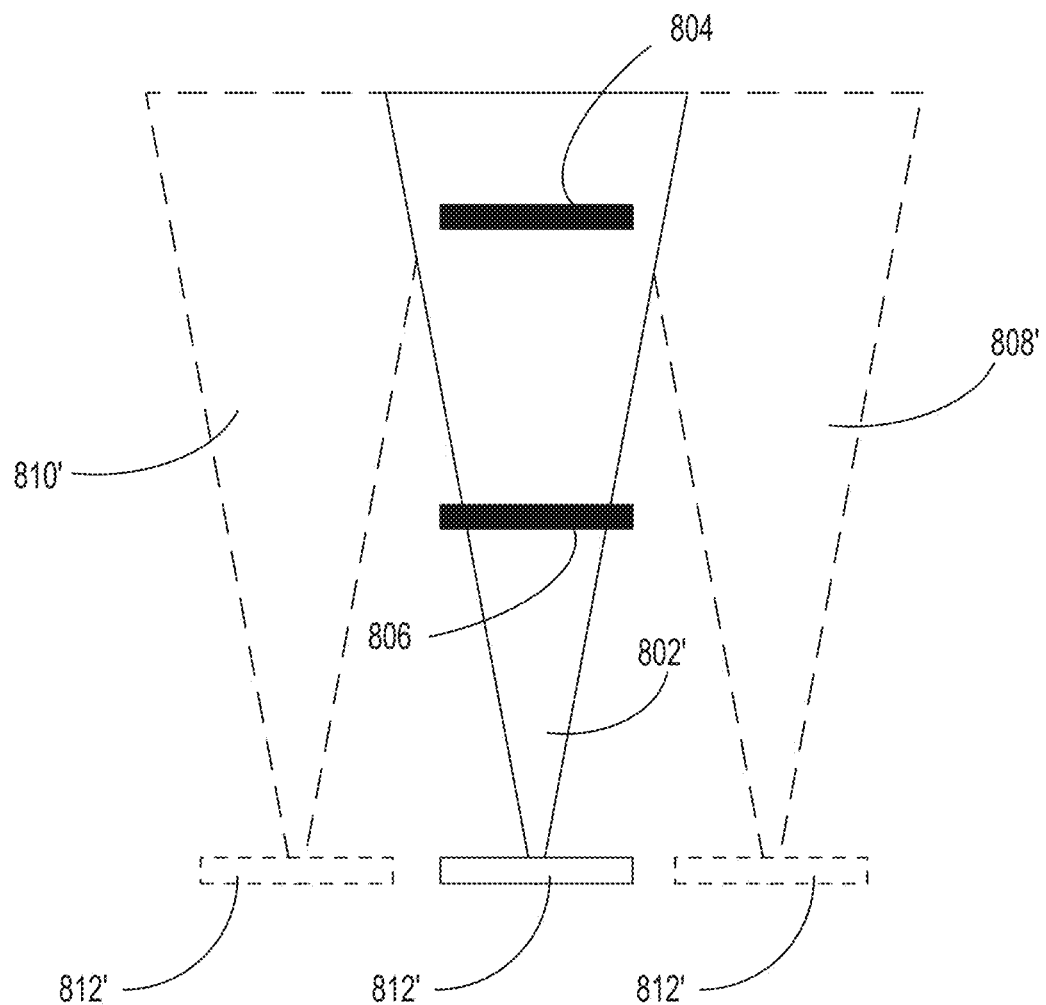
FIG. 8B shows a schematic view of an example arrangement of a plurality of temperature sensors, according to some embodiments.

FIGS. 8A and 8B depict one or more temperature sensor(s) that can be positioned at different viewing angles and/or positions while measuring temperature, according to embodiments. FIG. 8A depicts a sensor 812 that can be rotated about an axis (schematically depicted with arrow A) to scan across an opening of a toilet or other excretion collection device. The sensor 812, at each of the viewing angles, can have a FOV 802, 808, 810 that covers or spans a portion of the opening of the toilet or other excretion collection device. By rotating the sensor 812 between the various viewing angles, the sensor 812 can capture an object (e.g., urine and/or feces) that is being received through the opening of the toilet or other excretion collection device. Since a urine stream or feces can move, the rotation of the sensor 812 can be used to capture urine stream or feces regardless of the location that the urine and/or feces is being received through the opening. As depicted in FIG. 8A, objects 804, 806 (e.g., urine and/or feces) can be captured by the temperature sensor 812 in one of its many viewing angles. In some instances, an object 804 may only partially occupy the FOV of the sensor 812, while in other instances, an object 806 may occupy the entire FOV of the sensor 812.

FIG. 8B depicts an alternative arrangement of sensor(s) 812', where a sensor 812' can be translated linearly to various positions or a plurality of sensor(s) 812' can be positioned along a length of an opening of a toilet or other excretion collection device. As shown, in each of the positions, the sensor(s) 812' can have a FOV 802', 808', 810' that covers or spans a portion of the opening of the toilet or other excretion collection device. The temperature of objects 804, 806 (e.g., urine and/or feces) falling into the FOV of the temperature sensor(s) 812' can be captured by the temperature sensor(s) 812'. And similar to that described with reference to FIG. 8A, in some instances, an object 804 may only partially occupy the FOV of a sensor 812', while in other instances, an object 806 may occupy the entire FOV of a sensor 812'.

Figure 9A:
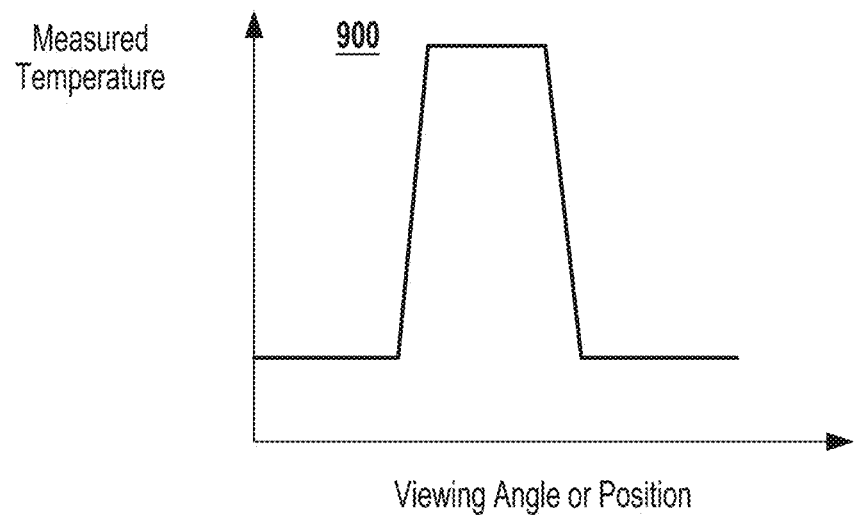
FIG. 9A shows an example temperature profile measured as a function of viewing angle or position of a temperature sensor, according to some embodiments.
Figure 9B:
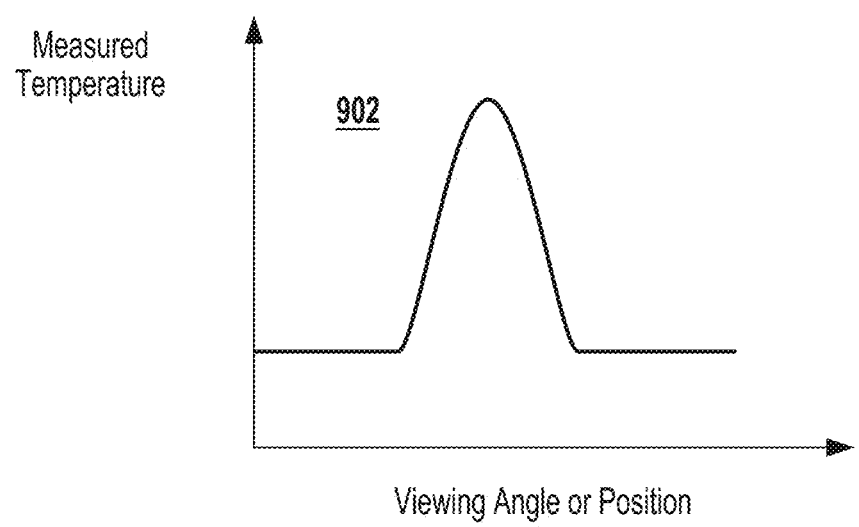
FIG. 9B shows an example temperature profile measured as a function of viewing angle or position of a temperature sensor, according to some embodiments.

The temperature measured by the sensors at its various viewing angles and/or positions (e.g., as depicted in FIGS. 8A and 8B) can be used to obtain a temperature profile, e.g., with respect to a degree of rotation of the sensor with the arrangement as depicted in FIG. 8A, or with respect to a relative position of the sensor with the arrangement as depicted in FIG. 8B. FIGS. 9A and 9B depict example temperature profiles of objects, as a function of viewing angle or position of the temperature sensor(s), according to some embodiments. Since a urine stream and/or feces typically has a temperature that is greater than its surroundings, the temperature profile of a urine stream and/or feces would have a peak associated with the urine stream and/or feces. When an object occupies the entire FOV of the temperature sensor (e.g., when a width of the object is greater than a diameter of the FOV of the sensor), then the temperature profile can have a pulse 900 with a plateau, as depicted in FIG. 9A. The temperature at the plateau can be representative of the temperature of the object, as other background object would not have affected the temperature measurement of the sensor. When an object does not occupy the entire FOV of the temperature sensor (e.g., when the width of the object is smaller than a diameter of the FOV of the sensor), then the temperature profile can have a pulse 902 without a plateau, as depicted in FIG. 9B. The peak temperature of the pulse 902 may not be representative of the temperature of the object, as other background objects may have affected the temperature measurement of the sensor. In such instances, an algorithm can be used to determine the temperature of the object, e.g., based on features that can be extracted from the pulse 902.

Since the temperature profile of an object can vary depending on whether that object occupies the entire FOV of a temperature sensor, it can be important to determine when an object is occupying the entire FOV of the sensor and when it is not. Returning back to FIG. 5, a temperature profile that is received at the processor (e.g., onboard processor (e.g., processor 120) and/or processor associated with an external compute device (e.g., user device 260, compute device 280)) can be evaluated, at 504, to determine whether the width of the object (e.g., urine or fecal) occupies an entire FOV of the temperature sensor when the sensor is in at least one angle or position. For example, the processor can determine whether the temperature profile has a plateau, and if the temperature profile has a plateau, then the processor can determine that the object occupied the entire FOV of the sensor (504: YES). Alternatively, if the temperature profile does not have a plateau, then the processor can determine that the object did not occupy the entire FOV of the sensor (504: NO). In some embodiments, determining whether the temperature profile has a plateau can include determining whether the temperature measured by the sensor(s) at different angles or positions are the same (or within a predefined value or percentage from one another), e.g., when the temperature measured by the sensor(s) at two or more positions are the same (or within a predefined value or percentage from one another).

Figure 13:
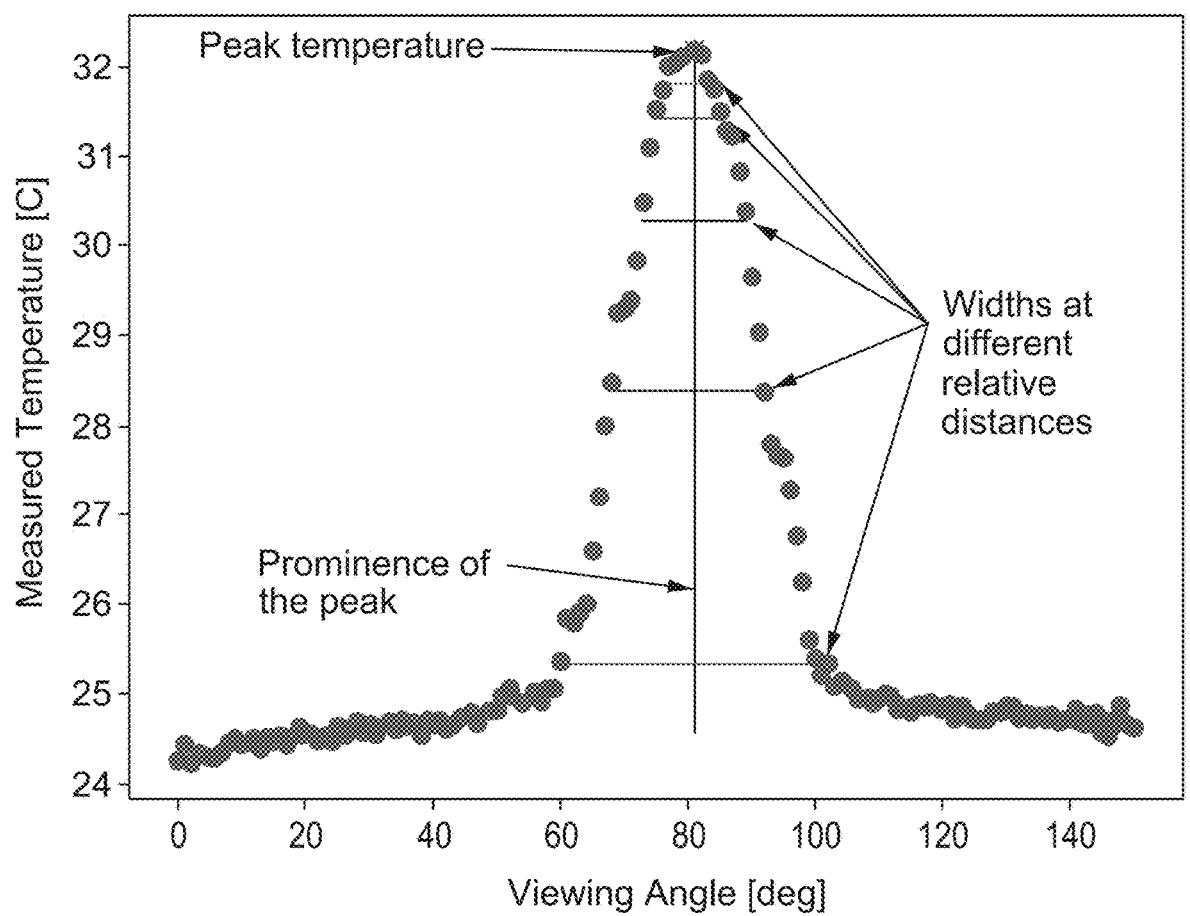
FIG. 13 is a plot of a temperature profile of an object, illustrating various parameters that can be extracted from the temperature profile, according to an embodiment.

Assuming that urine and/or feces would have a temperature that is greater than their surroundings, when the urine and/or feces occupies the entire FOV of the sensor(s) at one or more angles or positions (504: YES), then the processor can determine, at 506, the temperature of the object based on a maximum temperature that is measured by the sensor, e.g., a value of the plateau in the temperature profile. Alternatively, when the urine and/or feces occupies less than the entire FOV of the sensor(s) (504: NO), then the processor can extract features from the measured temperature profile, at 508, and input those extracted features into an algorithm (e.g., a trained machine learning model) to determine the temperature of the object, at 510. FIG. 13 depicts an example of a temperature profile 1300 measured by the temperature sensor when an object does not occupy an entire FOV of the sensor at any position or angle of the temperature sensor. In FIG. 13, the temperature measured by the sensor is plotted over a range of viewing angles of the temperature sensor (i.e., the range of angles through which the temperature sensor is rotated). The temperature profile 1300 can have a peak that is associated with the object. The maximum value of the peak, however, may not be representative of the temperature of the object because the object did not occupy the entire FOV of the sensor at any position or angle. As such, to determine the temperature of the object, certain features can be extracted from the temperature profile, including, for example, a maximum value of the peak, a width of the peak at different relative distances, a prominence of the peak (e.g., a difference between a baseline temperature or background temperature and a maximum temperature of the peak), etc. Such extracted features can then be input into a model or algorithm that is trained or calibrated to determine (e.g., predict) the temperature of the object based on the extracted features.

Figure 6:
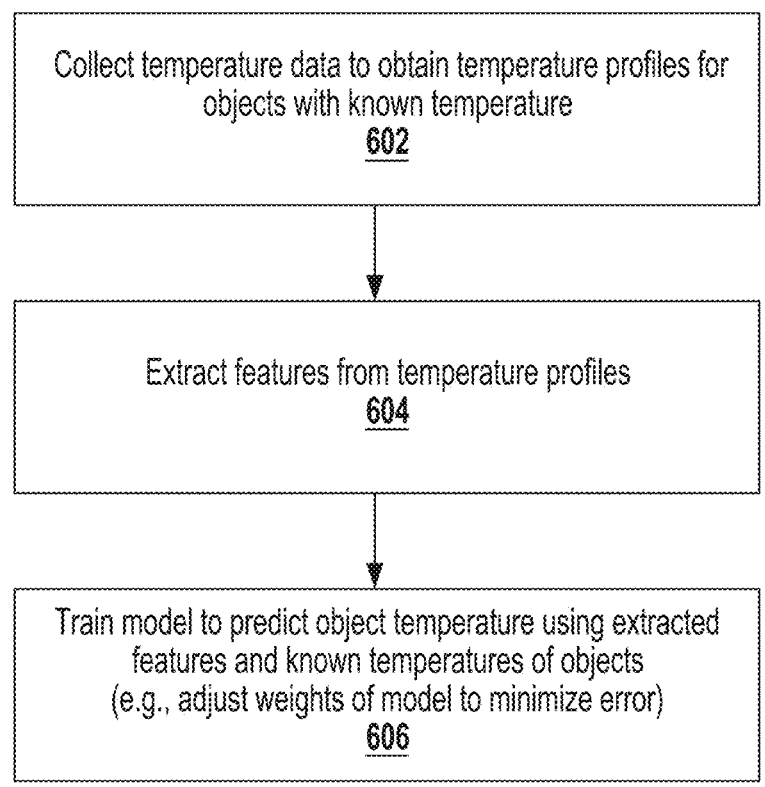
FIG. 6 is a flow chart of an example method of training a model used to determine a temperature of an object (e.g., feces and/or urine), according to an embodiment.

In some embodiments, a model (e.g., statistical model or machine learning model) that is calibrated using past temperature data can be used to determine the temperature of an object based on its temperature profile. FIG. 6 depicts an example method 600 for calibrating a model to determine the temperature of an object, according to embodiments. The method 600 can be performed by a processor coupled to any of the devices described herein (e.g., sensing device 100, 200, 300, 300', user device 260, compute device 280, third-party device 270). At 602, temperature data can be collected for objects with known temperature. In an embodiment, an experimental set-up, such as that described with reference to FIGS. 11A and 11B below, can be used to collect temperature data of objects with known temperature. To increase the accuracy of the model, the experimental set-up can be designed to replicate or be similar to a subject urinating or defecating into a toilet or other excretion collection device. For example, a sensing device or system (e.g., sensing device 100, 200, 300, 300') including one or more temperature sensors (e.g., temperature sensor(s) 112) can be coupled to a toilet or other excretion collection device, and the one or more temperature sensors can be used to measure the temperature of objects that are received through an opening of the toilet or other excretion collection device. The objects that are received can be, for example, urine streams and/or feces, solid materials of known temperature and/or surface characteristics (e.g., emissivity), or objects that approximate urine streams and/or feces (e.g., a stream of water). In some embodiments, the temperature sensor or an array of temperature sensors can be moved, e.g., translated linearly or rotated about an axis, to capture the temperature of objects being received through the opening of the toilet or other excretion collection device. The temperature data collected by the one or more temperature sensors can be used to generate a temperature profile for each object of known temperature.

The temperature profiles and the known temperatures of the objects can then be used to calibrate the model for predicting the temperatures of objects. The processor can extract features, such as, for example, peak temperature, peak widths (e.g., at different points along the peak), the prominence of the peak, etc., from the temperature profiles for each object, at 604. The extracted features can be input into the model, and the model can be calibrated or trained to output a value that is indicative of the known temperature of each object. The calibration can include adjusting one or more weights and/or parameters of the model to minimize an error between the predicted temperature output by the model and the known temperature of the object. In some embodiments, the model can include, for example, multiple linear regression, polynomial linear regression, support vector regression (SVR), decision tree regression, random forest regression, and/or artificial neural networks. Further details of calibrating a model using temperature data are provided below with reference to FIGS. 12 and 13.

Figure 10A:
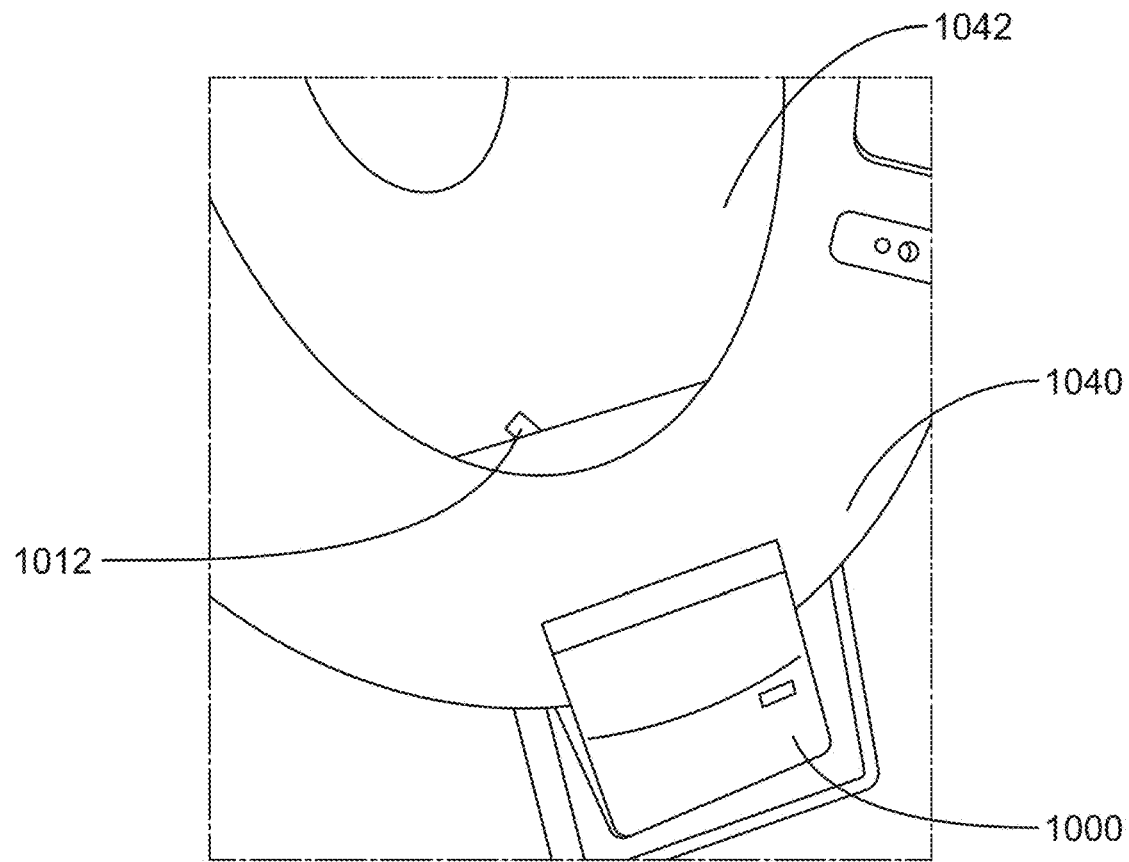
FIG. 10A shows a perspective view of a sensing device positioned with respect to a toilet seat, according to an embodiment.
Figure 10B:
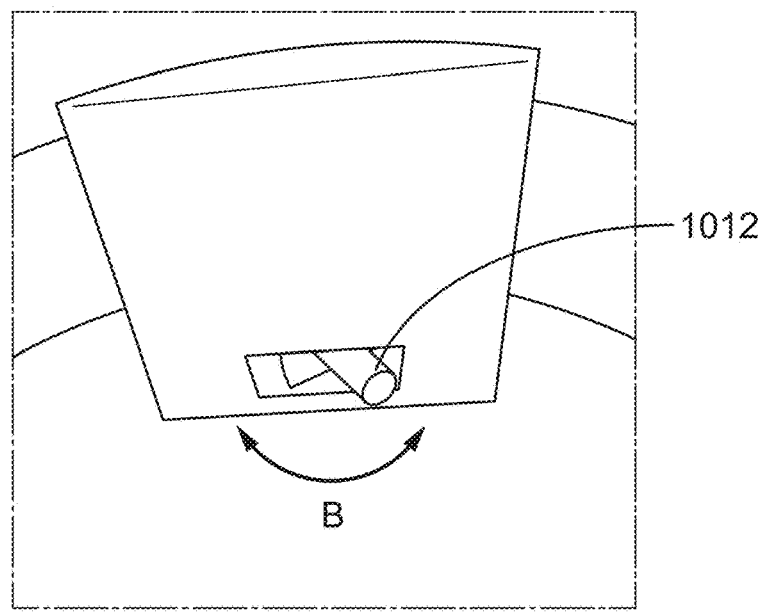
FIG. 10B shows a close-up view of a temperature sensor of a sensing device, according to an embodiment.

FIGS. 10A and 10B depict an example arrangement of a sensing device 1000 relative to an opening of a toilet, according to embodiments. FIG. 10A shows the sensing device 1000 attached to a front portion of a toilet seat 1040. The sensing device 1000 can include components that are structurally and/or functionally similar to other sensing devices described herein, including, for example, sensing device 100, 200, 300, 300'. The toilet seat 1040 can define an opening 1042 through which urine and/or feces can be received. The sensing device 1000 can include a temperature sensor 1012, which is directed toward the opening 1042 of the toilet seat 1040. In some embodiments, the sensing device 1000 can include a drive system (e.g., drive system 114) that is configured to move the temperature sensor 1012 such that the temperature sensor 1012 can scan at least a substantial portion of the opening 1042 of the toilet. For example, the sensing device 1000 can be configured to rotate the temperature sensor 1012, as illustrated by arrow B in FIG. 10B. The movement of the sensor can allow the sensor to capture objects (e.g., urine and/or feces) that are being received into the toilet at different locations along the opening 1042.

Figure 11A:
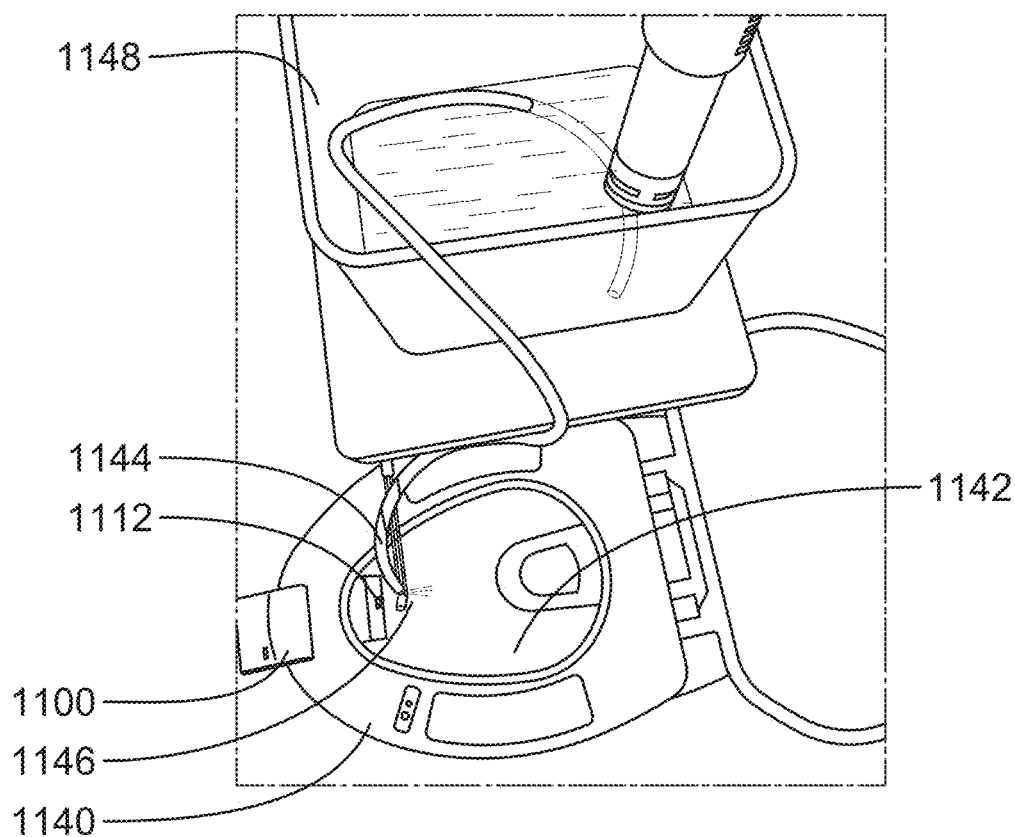
FIG. 11A shows an example set-up for testing of a temperature sensor of a sensing system, according to an embodiment.
Figure 11B:
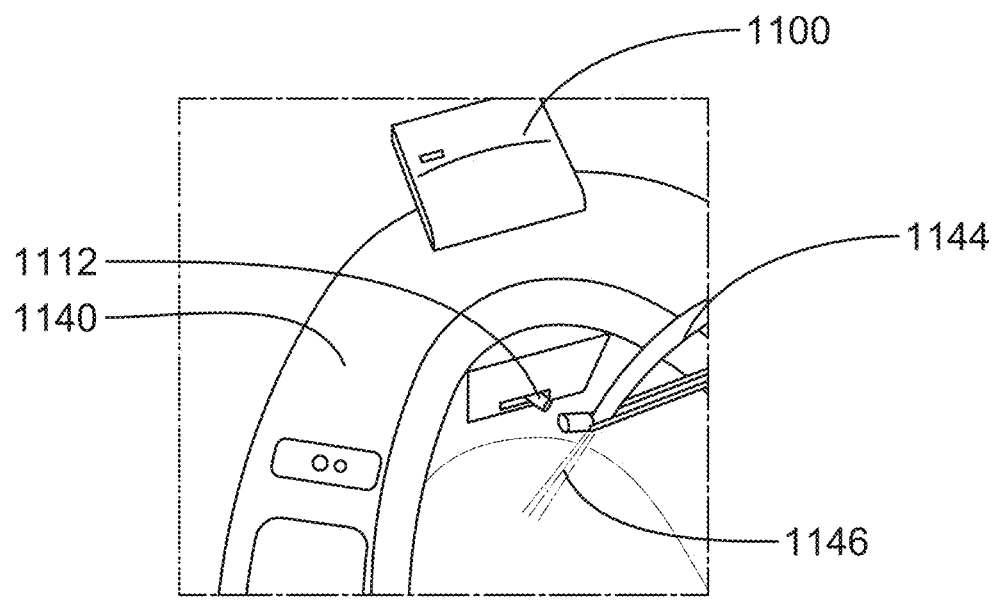
FIG. 11B shows a close-up view of the temperature sensor in the example set-up depicted in FIG. 11A.

FIGS. 11A-11B show an example experimental set-up for calibrating a temperature sensor 1112 of a sensing system 1100, according to embodiments. The sensing system 1100 can include components that are structurally and/or functionally similar to other sensing devices described herein, including, for example, sensing device 100, 200, 300, 300', 1000. The temperature sensor 1112 can be structurally and/or functionally similar to other temperature sensors described herein (e.g., temperature sensor(s) 112, 1012). The experimental set-up can be designed to simulate one or more urination/defecation events, which can be used to provide temperature data for training or calibrating a temperature prediction model.

In the experimental set-up, water in a water bath 1148 can be maintained at known, constant temperatures. In some embodiments, the water bath 1148 can be set to different temperatures in a range that generally corresponds to body temperature values, e.g., temperatures between about 36° C. to about 40° C. Water from the water bath 1148 can be discharged as a water stream 1146 into the toilet opening 1142 via a tube 1144. The water stream 1146 can simulate a urine stream being discharged from the body of an individual sitting on the toilet seat 1140. FIG. 11B shows a close-up view of the temperature sensor 1112 next to the water stream 1146. The water stream 1146 can have a known temperature (i.e., as set by the water bath 1148) and be discharged at a fixed distance from the temperature sensor 1112 of the sensing system 1100. To capture the temperature of the water stream 1146, the temperature sensor 1112 can be rotated about an axis with respect to the toilet seat 1140. The temperature measurements of the sensor 1112 can be used to obtain a temperature profile for the water stream 1146. This can be repeated for each water stream 1146 set at a known temperature. In a particular instance, the process of measuring temperature can be repeated for water streams having known temperatures of 36° C., 37° C., 38° C., 39° C., and 40° C.

The measured temperature profile for each water stream 1146 can vary depending on, for example, the temperature of the water stream as well as the background temperature of the toilet, the width of the water stream, the distance that the water stream is from the sensor 1112, etc. The temperature profiles can be used to train or calibrate a model to predict the temperature of an object (e.g., urine and/or feces) being deposited into a toilet, e.g., as described with reference to FIG. 6. In some instances, the experimental set-up can be varied to capture other factors or variables that may impact the ability of the system to determine the temperature of urine and/or feces. For example, in different variations of the testing set-up, the water stream 1146 can be discharged at different positions in the toilet bowl and at different distances from the temperature sensor. These variations can be used to generate different temperature profiles corresponding to various situations that may occur in actual urination/defecation events. As such, a large variety of experimental set-ups that produce different temperature profiles for water streams 1146 having known temperatures and/or other properties can be used to effectively train or calibrate a temperature prediction model.

While an experimental set-up using a water bath is shown in FIGS. 11A-11B, it can be appreciated that other experimental set-ups can be used to approximate a urination and/or defecation event and provide temperature data that can be used to calibrate a temperature prediction model. For example, in an alternative arrangement, the temperature data can be gathered using a blackbody source along with a barrier having an empty slot at its center for simulating a urine stream. The blackbody source can then be set to different temperatures to obtain different temperature profiles.

Figure 12:
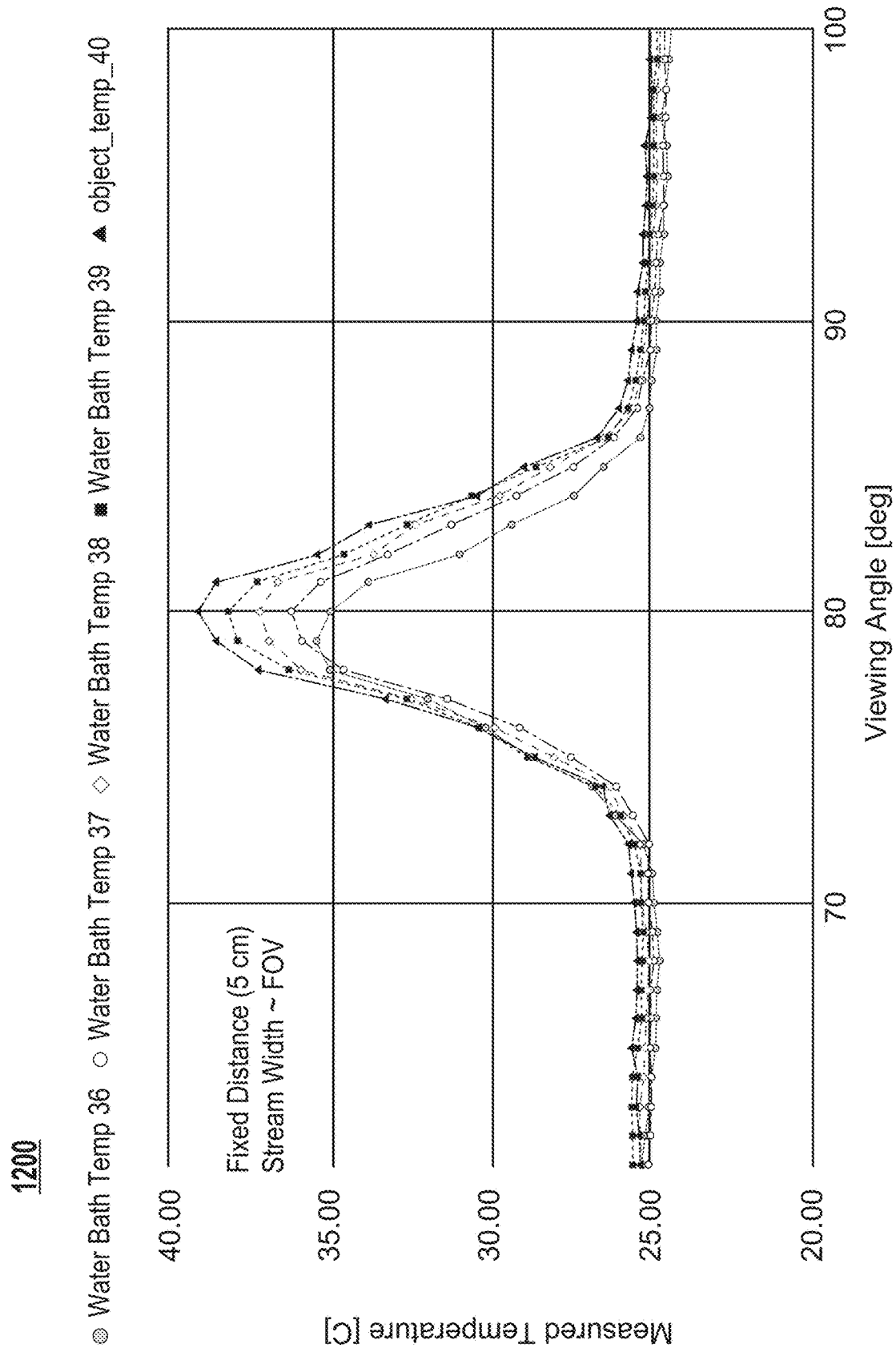
FIG. 12 is a plot of temperature profiles measured by the temperature sensor as a function of viewing angle of the temperature sensor as depicted in the set-up of FIGS. 11A-11B, according to an embodiment.

FIG. 12 is a plot 1200 of temperature profiles of temperature data measured by a temperature sensor (e.g., temperature sensor 1112) as a function of a viewing angle of the temperature sensor. The plot 1200 includes the temperature profiles of water streams set to five different temperatures—specifically, 36° C., 37° C., 38° C., 39° C., and 40° C. The temperature data for each temperature profile can be provided over a range of viewing angles—specifically, from about 60° to about 100° relative to a starting position of the sensor. As depicted in FIG. 12, the temperature profiles do not have a plateau and therefore may have a peak temperature that is not representative of the temperature of the water streams (e.g., due to the water streams having a smaller width than the sensor's FOV).

Features can be extracted from the temperature profiles provided in FIG. 12 and used to calibrate a model to predict the temperature of an object. For example, as shown in FIG. 13, various features of a temperature profile 1300 can be extracted, including, for example:

(1) Maximum peak temperature of the temperature profile.

(2) Prominence of the peak or the amount the peak stands out from its surrounding baseline, e.g., a vertical distance between the maximum peak temperature and a lowest contour line of the temperature profile.

(3) The width of the peak at different relative distances to the peak's height and prominence. For example, the width of the peak can be measured at temperature values corresponding to about 1%, about 5%, about 10%, about 25%, about 50%, about 90%, and about 99% of the peak's prominence from the baseline temperature value (inclusive of all values and ranges therebetween).

(4) The area under the curve between the peak's lowest contour or baseline and data points having a higher temperature than that corresponding to the peak's lowest contour.

(5) Background temperature or baseline temperature. With the measurements being done inside a toilet bowl with a constant background, the background temperature would be generally uniform across the recorded temperature profiles, and the emissivity of the background would also be constant due to the consistent material in the background.

(6) Ambient temperature, e.g., as measured separately by a temperature sensor (e.g., additional sensor(s) 113 in the housing 110 as shown in FIG. 1).

Parameters other than those extracted from the temperature profile can also be used to calibrate a temperature prediction model, such as, for example, the sampling rate of the temperature sensor, the scanning speed of the temperature sensor, and the position of the sensor relative to the target object (e.g., water stream or blackbody source), etc. For example, a higher scanning rate requires a higher sampling rate of the sensor. A higher sampling rate can also reduce the error originating from the movement of the target object. However, increasing the sampling rate may decrease the accuracy of the measurement. The optimization of these parameters along with the position of the sensor can improve the accuracy of predicting the temperature using various models.

Various models can be used to predict the temperature of an object based on a temperature profile (or features extracted from a temperature profile). Example models include multiple linear regression, polynomial linear regression, SVR, decision tree regression, random forest regression, and artificial neural networks. Table 2 below shows the performance metrics of various models that were calibrated using temperature profile data of known temperature sources (e.g., water steams or black body sources with known temperatures). As shown, of the models calibrated using the temperature data, the multiple linear regression model shows the best fitting results with a coefficient of determination of 0.9 and a maximum absolute error of 0.79° C.

TABLE 2

| Model | R2 for the test dataset [C] | Max absolute error [C] | Error standard deviation [C] |
|---|---|---|---|
| SVR 1 | 0.91 | 0.79 | 0.15 |
| Linear regression 1 | 0.90 | 1.63 | 0.29 |
| Random forest 1 | 0.79 | 1.79 | 0.34 |
| ANN 1 | 0.91 | 2.10 | 0.33 |
| Polynomial regression 1 | 0.93 | 0.98 | 0.18 |
| Decision tree | 0.60 | 1.92 | 0.36 |

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The invention claimed is:

1. A system, comprising:
a set of force sensors disposed about a ring of a toilet, the set of force sensors configured to collectively measure forces present on the ring when a subject is seated on the ring;
a non-contact temperature sensor orientated toward an opening of the toilet;
a drive system coupled to the non-contact temperature sensor, the drive system configured to rotate the non-contact temperature sensor about an axis to scan laterally across a substantial majority of the opening, the non-contact temperature sensor configured to measure temperature data while rotating to scan laterally across the substantial majority of the opening and as urine or feces of the subject is received through the opening; and
a processor operatively coupled to the set of force sensors and the non-contact temperature sensor, the processor configured to receive signals indicative of the forces measured by the set of force sensors and the temperature data and to determine, using the signals and the temperature data, at least a subset of a weight, a ballistocardiogram (BCG), a posture, or a core body temperature of the subject.

2. The system of claim 1, wherein the processor is disposed on or about the toilet.

3. The system of claim 1, wherein the set of force sensors and the non-contact temperature sensor are integrated into the ring.

4. The system of claim 1, wherein the non-contact temperature sensor is supported on a housing that includes a coupler configured to mechanically couple to the ring.

5. The system of claim 1, wherein the processor is configured to determine the weight, the BCG, or the posture of the subject using the signals indicative of the forces measured by the set of force sensors and to determine the core body temperature using the temperature data.

6. The system of claim 1, further comprising a sensor configured to detect that the subject is seated on the ring,
the processor further configured to, in response to the sensor detecting that the subject is seated on the ring, activate the drive system to rotate the non-contact temperature sensor such that the non-contact temperature sensor measures the temperature data of the urine or feces.

7. The system of claim 1, further comprising a communication interface configured to send signals indicative of the core body temperature of the subject to a processor of a compute device such that the processor of the compute device, in response to receiving the signals, assesses one or more physiological conditions of the subject based on the core body temperature.

8. The system of claim 1, wherein the non-contact temperature sensor includes an array of non-contact temperature sensors configured to span the substantial majority of the opening of the toilet such that the array of non-contact temperature sensors can measure the temperature data of the urine or feces.

9. The system of claim 1, further comprising a sensor configured to detect a urination or defecation event,
the processor further configured to, in response to the sensor detecting the urination or defecation event, activate the drive system to rotate the non-contact temperature sensor such that the non-contact temperature sensor measures the temperature data of the urine or feces.

10. A system, comprising:
a set of force sensors disposed about a ring of a toilet, the set of force sensors configured to collectively measure forces present on the ring when a subject is seated on the ring;
a housing;
a non-contact temperature sensor supported by the housing, the non-contact temperature sensor including an infrared (IR) thermometer oriented towards an opening of the toilet;
a drive system coupled to the non-contact temperature sensor, the drive system configured to move the non-contact temperature sensor to scan laterally across a substantial majority of the opening, the non-contact temperature sensor configured to measure temperature data while being moved by the drive system to scan laterally across the substantial majority of the opening and as urine or feces of the subject is received through the opening; and
a processor operatively coupled to the set of force sensors and the non-contact temperature sensor, the processor configured to:
receive the temperature data and combine the temperature data into a temperature profile representing temperature measured across different spatial positions corresponding to the substantial majority of the opening, the temperature profile including temperature indicative of one or more objects within the area scanned by non-contact the temperature sensor;
extract a set of features from the temperature profile; and
determine, using a model trained to predict core body temperature, a core body temperature of the subject based on the extracted features.

11. The system of claim 10, wherein the processor is further configured to receive signals indicative of the forces measured by the set of force sensors; and determine, using the signals, a weight, a ballistocardiogram (BCG), or a posture of the subject.

12. The system of claim 11, further comprising a sensor configured to detect that the subject is seated on the ring,
the processor further configured to, in response to the sensor detecting that the subject is seated on the ring, activate the non-contact temperature sensor to measure the temperature data of the urine or feces.

13. The system of claim 10, wherein the model includes one or more of: multiple linear regression, polynomial linear regression, support vector regression (SVR), decision tree regression, random forest regression, or artificial neural networks.

14. The system of claim 10, wherein the extracted set of features includes at least on of: a maximum peak temperature, a prominence of the peak temperature, a width of the peak temperature at a predetermined distance from the peak temperature height, or an area under a curve between a temperature baseline and data points having a higher temperature than that corresponding to the temperature baseline.

15. The system of claim 10, wherein the system further comprises a communication interface configured to send a signal indicative of the core body temperature to a processor of a compute device, such that the processor of the compute device, in response to receiving the signal, assesses one or more physiological conditions of the subject based on at least the core body temperature.

16. The system of claim 10, wherein the drive system is configured to rotate the non-contact temperature sensor about an axis to scan laterally across the substantial majority of the opening.

17. The system of claim 10, further comprising a sensor configured to detect an urination or defecation event,
the processor further configured to, in response to the sensor detecting the urination or defecation event, activate the drive system to move the non-contact temperature sensor such that the non-contact temperature sensor measures the temperature data of the urine or feces.

18. The system of claim 10, wherein the housing is integrated into the ring of the toilet.

19. The system of claim 10, wherein the housing includes a coupler configured to mechanically couple to the ring.

20. The system of claim 10, wherein the model is configured to predict the temperature of the urine or feces using previously collected temperature profiles of objects with known temperatures.

21. The system of claim 10, wherein the set of features include at least one of: a peak maximum value, a peak width, or a prominence of a peak.

22. The system of claim 10, wherein the non-contact temperature sensor is calibrated to have an accuracy of between about 0.05° C. and about 1° C. within a range of temperatures of between about 20° C. and about 40° C.

23. A system, comprising:
a set of force sensors disposed about a ring of a toilet, the set of force sensors configured to collectively measure forces present on the ring when a subject is seated on the ring;
a non-contact temperature sensor oriented toward an opening of the toilet;
a drive system coupled to the non-contact temperature sensor, the drive system configured to move the non-contact temperature sensor such that the non-contact temperature sensor measures, while being moved by the drive system, temperature data associated with a urine stream or feces of the subject before the urine stream or feces contacts the toilet; and
a processor operatively coupled to the set of force sensors and the non-contact temperature sensor, the processor configured to receive signals indicative of the forces measured by the set of force sensors and the temperature data and to determine, using the signals and the temperature data, a ballistocardiogram (BCG) and a core body temperature of the subject.

24. The system of claim 23, wherein the processor is disposed on or about the toilet.

25. The system of claim 23, wherein the set of force sensors and the non-contact temperature sensor are integrated into the ring.

26. The system of claim 23, wherein the non-contact temperature sensor is supported on a housing that includes a coupler configured to mechanically couple to the ring.

27. The system of claim 23, wherein the drive system is configured to rotate the non-contact temperature sensor about an axis to measure the temperature data.

28. The system of claim 23, wherein the drive system is configured to linearly translate the non-contact temperature sensor to measure the temperature data.

29. The system of claim 23, further comprising a sensor configured to detect that the subject is seated on the ring,
the processor further configured to, in response to the sensor detecting that the subject is seated on the ring, activate the drive system to rotate the non-contact temperature sensor such that the non-contact temperature sensor measures the temperature data.

30. The system of claim 23, wherein the non-contact temperature sensor includes an array of non-contact temperature sensors.

31. A system, comprising:
a sensor configured to detect when a subject is seated on a ring of a toilet;
a set of force sensors disposed about the ring of the toilet, the set of force sensors configured to collectively measure forces present on the ring when the subject is seated on the ring;
a non-contact temperature sensor orientated toward an opening of the toilet;
a drive system coupled to the non-contact temperature sensor, the drive system configured to move the non-contact temperature sensor to scan laterally across a substantial majority of the opening, the non-contact temperature sensor configured to measure temperature data while scanning laterally across the substantial majority of the opening area and as urine or feces of the subject is received through the opening; and
a processor operatively coupled to the sensor, the set of force sensors, and the non-contact temperature sensor, the processor configured to:
receive signals indicative of the sensor detecting that the subject is seated on the ring;
activate, in response to the sensor detecting that the subject is seated on the ring, the drive system to move the non-contact temperature sensor such that the non-contact temperature sensor measures the temperature of the urine or feces;
receive signals indicative of the forces measured by the set of force sensors and the temperature data; and
determine, using the signals indicative of the forces measured by the set of force sensors and the temperature data, a ballistocardiogram (BCG), and a core body temperature of the subject.

32. The system of claim 31, wherein the drive system is configured to rotate the non-contact temperature sensor about an axis to scan laterally across the substantial majority of the opening.

33. The system of claim 31, wherein the drive system is configured to linearly translate the non-contact temperature sensor to scan laterally across the substantial majority of the opening.

34. The system of claim 31, wherein the processor is disposed on or about the toilet.

35. The system of claim 31, wherein the sensor configured to detect when the subject is seated on the ring of the toilet includes a motion sensor, a light sensor, or a force sensor.

36. The system of claim 31, wherein the sensor, the set of force sensors and the non-contact temperature sensor are integrated into the ring.

37. The system of claim 31, further comprising a communication interface configured to send signals indicative of the core body temperature of the subject to a processor of a compute device such that the processor of the compute device, in response to receiving the signals, assesses one or more physiological conditions of the subject based on the core body temperature.

38. The system of claim 31, wherein the non-contact temperature sensor includes an array of non-contact temperature sensors configured to span the substantial majority of the opening of the toilet such that the array of non-contact temperature sensors can measure the temperature data of the urine or feces.

* * * * *